United States Patent
Horowitz

(10) Patent No.: US 10,244,239 B2
(45) Date of Patent: Mar. 26, 2019

(54) PARAMETER SET FOR PICTURE SEGMENTATION

(75) Inventor: Michael Horowitz, Austin, TX (US)

(73) Assignee: Dolby Laboratories Licensing Corporation, San Francisco, CA (US)

( * ) Notice: Subject to any disclaimer, the term of this patent is extended or adjusted under 35 U.S.C. 154(b) by 470 days.

(21) Appl. No.: 13/336,675

(22) Filed: Dec. 23, 2011

(65) Prior Publication Data

US 2012/0163453 A1     Jun. 28, 2012

Related U.S. Application Data

(60) Provisional application No. 61/427,569, filed on Dec. 28, 2010.

(51) Int. Cl.
*H04N 19/137*     (2014.01)
*H04N 7/12*     (2006.01)
(Continued)

(52) U.S. Cl.
CPC ......... *H04N 19/139* (2014.11); *H04N 19/103* (2014.11); *H04N 19/105* (2014.11); *H04N 19/117* (2014.11); *H04N 19/137* (2014.11); *H04N 19/159* (2014.11); *H04N 19/172* (2014.11); *H04N 19/174* (2014.11); *H04N 19/196* (2014.11); *H04N 19/436* (2014.11);
(Continued)

(58) Field of Classification Search
CPC ........ H04N 7/26; H04N 11/04; H04N 19/176; H04N 7/30; H04N 19/137; H04N 19/172; H04N 19/436; H04B 1/66

USPC ........... 375/240.24, 240.15, 240.02, 240.12, 375/240.08, 240.01–240.09; 382/243, 382/240
See application file for complete search history.

(56) References Cited

U.S. PATENT DOCUMENTS

| | | |
|---|---|---|
| 4,949,388 A | 8/1990 | Bhaskaran |
| 5,638,128 A | 6/1997 | Hoogenboom et al. |

(Continued)

FOREIGN PATENT DOCUMENTS

| | | |
|---|---|---|
| CA | 2314333 | 1/2002 |
| CN | 1286572 | 3/2001 |

(Continued)

OTHER PUBLICATIONS

Sullivan et al., Overview of the High Efficiency Video Coding (HEVC) Standard, IEEE Transactions on Circuits and Systems for Video Technology, vol. 22, No. 12, Dec. 2012.*

(Continued)

*Primary Examiner* — Albert Kir

(57) ABSTRACT

Systems and methods for picture segmentation through columns and slices in video encoding and decoding. A video picture is divided into a plurality of columns, each column covering only a part of the video picture in a horizontal dimension. All coded tree blocks ("CTBs") belonging to a slice may belong to one or more columns. The columns may be used to break the same or different prediction or in-loop filtering mechanisms of the video coding, and the CTB scan order used for encoding and/or decoding may be local to a column. Column widths may be indicated in a parameter set and/or may be adjusted at the slice level. At the decoder, column width may be parsed from the bitstream, and slice decoding may occur in one or more columns.

23 Claims, 8 Drawing Sheets

(51) Int. Cl.
| | |
|---|---|
| H04N 19/44 | (2014.01) |
| H04N 19/139 | (2014.01) |
| H04N 19/105 | (2014.01) |
| H04N 19/70 | (2014.01) |
| H04N 19/46 | (2014.01) |
| H04N 19/61 | (2014.01) |
| H04N 19/117 | (2014.01) |
| H04N 19/174 | (2014.01) |
| H04N 19/82 | (2014.01) |
| H04N 19/436 | (2014.01) |
| H04N 19/91 | (2014.01) |
| H04N 19/159 | (2014.01) |
| H04N 19/196 | (2014.01) |
| H04N 19/50 | (2014.01) |
| H04N 19/80 | (2014.01) |
| H04N 19/103 | (2014.01) |
| H04N 19/172 | (2014.01) |

(52) U.S. Cl.
CPC ............. *H04N 19/44* (2014.11); *H04N 19/46* (2014.11); *H04N 19/50* (2014.11); *H04N 19/61* (2014.11); *H04N 19/70* (2014.11); *H04N 19/80* (2014.11); *H04N 19/82* (2014.11); *H04N 19/91* (2014.11)

(56) References Cited

U.S. PATENT DOCUMENTS

| | | | |
|---|---|---|---|
| 5,724,451 A * | 3/1998 | Shin et al. | 382/240 |
| 5,995,167 A | 11/1999 | Fukushima et al. | |
| 6,263,023 B1 | 7/2001 | Ngai | |
| 7,162,093 B2 | 1/2007 | Regunathan et al. | |
| 8,831,097 B2 * | 9/2014 | Jung et al. | 375/240.12 |
| 8,995,525 B2 | 3/2015 | Wiegand | |
| 9,060,174 B2 | 6/2015 | Horowitz | |
| 9,313,505 B2 | 4/2016 | Horowitz | |
| 9,369,722 B2 | 6/2016 | Horowitz | |
| 9,794,573 B2 | 10/2017 | Horowitz | |
| 2002/0071489 A1 | 6/2002 | Ramanzin | |
| 2004/0101059 A1 | 5/2004 | Joch et al. | |
| 2005/0008079 A1 | 1/2005 | Boon et al. | |
| 2005/0008240 A1 | 1/2005 | Banerji et al. | |
| 2005/0053158 A1 | 3/2005 | Regunathan et al. | |
| 2005/0141620 A1 | 6/2005 | Hattori | |
| 2005/0286634 A1 | 12/2005 | Duvivier | |
| 2006/0115001 A1 * | 6/2006 | Wang et al. | 375/240.24 |
| 2006/0146734 A1 | 7/2006 | Wenger et al. | |
| 2007/0104269 A1 | 5/2007 | Xue et al. | |
| 2007/0280346 A1 | 12/2007 | Tue et al. | |
| 2007/0291978 A1 | 12/2007 | Kim et al. | |
| 2008/0151997 A1 | 6/2008 | Oguz | |
| 2008/0170629 A1 | 7/2008 | Shim et al. | |
| 2008/0219349 A1 * | 9/2008 | Huang et al. | 375/240.15 |
| 2008/0267287 A1 | 10/2008 | Hannuksela | |
| 2009/0010331 A1 | 1/2009 | Jeon et al. | |
| 2009/0010334 A1 * | 1/2009 | Ueda et al. | 375/240.15 |
| 2009/0028448 A1 | 1/2009 | Colomosse et al. | |
| 2009/0141814 A1 | 6/2009 | Yin | |
| 2009/0304086 A1 | 12/2009 | Shi | |
| 2009/0316793 A1 | 12/2009 | Yang et al. | |
| 2009/0323809 A1 | 12/2009 | Raveendran | |
| 2010/0128797 A1 * | 5/2010 | Dey | H04N 19/176 375/240.24 |
| 2010/0128803 A1 | 5/2010 | Divorra Escoda et al. | |
| 2010/0158401 A1 * | 6/2010 | Shiraishi et al. | 382/243 |
| 2010/0296585 A1 * | 6/2010 | Shiraishi et al. | 382/243 |
| 2010/0189181 A1 | 7/2010 | Zheng et al. | |
| 2010/0303153 A1 | 12/2010 | Kadono | |
| 2011/0116545 A1 | 5/2011 | Zan | |
| 2012/0044994 A1 | 2/2012 | Suzuki | |
| 2012/0082244 A1 | 4/2012 | Chen et al. | |
| 2012/0106622 A1 * | 5/2012 | Huang | H04N 19/129 375/240.01 |
| 2012/0106629 A1 * | 5/2012 | Zheng et al. | 375/240.02 |
| 2012/0163452 A1 | 6/2012 | Horowitz | |
| 2015/0092842 A1 | 4/2015 | Horowitz | |
| 2015/0237352 A1 | 8/2015 | Horowitz | |
| 2015/0245025 A1 | 8/2015 | Horowitz | |

FOREIGN PATENT DOCUMENTS

| | | |
|---|---|---|
| CN | 1397138 | 2/2003 |
| CN | 1477852 | 2/2004 |
| CN | 1774934 | 5/2006 |
| CN | 1965321 | 5/2007 |
| CN | 101325698 | 12/2008 |
| CN | 101490968 | 7/2009 |
| CN | 101543076 | 9/2009 |
| CN | 101740082 | 6/2010 |
| WO | WO03094530 | 11/2003 |
| WO | WO2008057308 A3 | 2/2009 |
| WO | WO2010039731 | 4/2010 |

OTHER PUBLICATIONS

JCT-VC, "Test Model Under Consideration", Apr. 15, 2010.*
International Bureau of WIPO, International Search Report and Written Opinion of the International Searching Authority dated Mar. 20, 2012, issued in respect of International Application No. PCT/CA2011/001411.
Dhont et al.; Flexible macroblock ordering as a content adaptation tool in H264/AVC; Proceedings of the SPIE, vol. 6015, pp. 601506-1-601506-9; Oct. 24, 2005.
European Search Report issued in EP11852303.4 dated Jun. 2, 2015, 6 pages.
International Bureau of WIPO, International Search Report and Written Opinion of International Searching Authority dated Apr. 17, 2012, issued in respect of International Application No. PCT/CA2011/001412, 10 pages.
International Preliminary Report on Patentability in International Application No. PCT/CA2011/001412, dated Jul. 2, 2013, 7 pages.
International Preliminary Report on Patentability in International Application No. PCT/CA2011/001411, dated Jul. 2, 2013, 5 pages.
Bossen, "Common test conditions and software reference configurations," JCT-VC Document JCTVC-B300, Geneva, Jul. 2010, 12 pages.
ITU-T Recommendation H.263 version 2 (H.263+), "Video coding for low bit rate communication," 1998, 167 pages.
ITU-T Recommendation H.264 and ISO/IEC 14496-10, "Advanced Video Coding for Generic Audiovisual Services," (Mar. 2010), 676 pages.
JCT-VC, "Test Model under Consideration Software 0.9-ahg-slices," retrieved on Dec. 11, 2014, retrieved from the Internet: URL: https://hevc.hhi.fraunhofer.de/svn/svn_HEVCSoftware/branches/0.9-ahg-slices/, 1 page.
Misra et al., "Entropy slices for parallel entropy coding," JCT-VC Document, JCTVC-C256, Guangzhou, Oct. 2010, 6 pages.
Sjoberg and Wennersten, "Fine granularity slices," JCT-VC Document, JCTVC-C154, Guangzhou, Oct. 2010, 4 pages.
Wenger and Horowitz, "Flexible Macroblock ordering (FMO)," JVT-0089, May 2002, 22 pages.
Zhou, "Sub-picture based raster scanning coding order for HEVC UHD video coding," JCTVC-B062, Geneva, Jul. 2010, 4 pages.
Wang et al., "Dependency and loop filtering control over tile boundaries," Document: JCTVC-G317, JCT-VC of ITU-T SG16 WP3 and ISO/IEC JTC1/SC29/WG11, 7th Meeting: Geneva, CH, Nov. 21-30, 2011, 7 pages.
Office Action issued in Chinese Application No. 201180062300.7 dated Oct. 10, 2015, 17 pages (with English translation).
Office Action issued in Chinese Application No. 201180062299.8 dated Nov. 18, 2015, 14 pages (with English translation).
Office Action Issued in Chinese Application No. 201180062299.8 dated May 3, 2016, 14 pages (with English Translation).
Office Action issued in EP11853888.3 dated Mar. 21, 2016, 5 pages.
European Office Action issued in European Application No. 11853888.3, dated Apr. 11, 2018, 11 pages.

(56) References Cited

OTHER PUBLICATIONS

CN Office Action in Chinese Appln No. 201611033822.5, dated Oct. 10, 2018, 19 pages.
CN Office Action in Chinese Appln. No. 201611033819.3, dated Nov. 2, 2018, 20 pages.
CN Office Action in Chinese Appln. No. 201611033820.6, dated Nov. 26, 2018, 14 pages.

* cited by examiner

| 0 | 1 | 2 | 3 | 4 | 5 | 6 | 7 | 8 | 9 |
|---|---|---|---|---|---|---|---|---|---|
| 10 | 11 | 12 | 13 | 14 | 15 | 16 | 17 | 18 | 19 |
| 20 | 21 | 22 | 23 | 24 | 25 | 26 | 27 | 28 | 29 |
| 30 | 31 | 32 | 33 | | | | | | |
| 40 | 41 | | | | | | | | |
| 50 | 51 | | | | | | | | |

FIG. 5  500

PARAMETER SET FOR PICTURE SEGMENTATION

CROSS-REFERENCE TO RELATED APPLICATIONS

This application claims priority from U.S. Provisional Patent Application Ser. No. 61/427,569, filed Dec. 28, 2010, entitled "PICTURE SEGMENTATION USING GENERALIZED SLICES", the entire contents of which are incorporated herein by reference.

FIELD

Embodiments of the invention relate to video coding, and more specifically to the segmentation of a coded picture into one or more columns and slices.

BACKGROUND

Digital video capabilities can be incorporated into a wide range of devices, including digital televisions, digital direct broadcast systems, wireless broadcast systems, personal digital assistants (PDAs), laptop or desktop computers, video cameras, digital recording devices, video gaming devices, video game consoles, cellular or satellite radio telephones, and the like. Digital video devices may implement video compression techniques, such as those described in standards like MPEG-2, MPEG-4, both available from the International Organization for Standardization ("ISO") 1, ch. de la Voie-Creuse, Case postale 56, CH-1211 Geneva 20, Switzerland, or www.iso.org, or ITU-T H.264/MPEG-4, Part 10, Advanced Video Coding ("AVC"), available from the International Telecommunication Union ("ITU"), Place de Nations, CH-1211 Geneva 20, Switzerland or www.itu.int, each of which is incorporated herein by reference in their entirety, or according to other standard or non-standard specifications, to encode and/or decode digital video information efficiently.

A video encoder can receive uncoded video information for processing in any suitable format, which may be a digital format conforming to ITU-R BT 601 (available from the International Telecommunications Union, Place des Nations, 1211 Geneva 20, Switzerland, www.itu.int, and which is incorporated herein by reference in its entirety) or in some other digital format. The uncoded video may be organized both spatially into pixel values arranged in one or more two-dimensional matrices as well as temporally into a series of uncoded pictures, with each uncoded picture comprising one or more of the above-mentioned two-dimensional matrices of pixel values. Further, each pixel may comprise a number of separate components used to represent color in digital format. One common format for uncoded video that is input to a video encoder has, for each group of four pixels, four luminance samples which contain information regarding the brightness/lightness or darkness of the pixels, and two chrominance samples which contain color information (e.g., YCrCb 4:2:0).

One function of video encoders is to translate (more generally "transform") uncoded pictures into a bitstream, packet stream, NAL unit stream, or other suitable transmission format (all referred to as "bitstream" henceforth), with goals such as reducing the amount of redundancy encoded into the bitstream to thereby increase transmission rates, increasing the resilience of the bitstream to suppress bit errors or packet erasures that may occur during transmission (collectively known as "error resilience"), or other application-specific goals. Embodiments of the present invention provided for at least one of the removal or reduction of redundancy, the increase in error resilience, and implementability of video encoders and/or associated decoders in parallel processing architectures.

One function of video decoders is to receive as its input a coded video in the form of a bitstream that may have been produced by a video encoder conforming to the same video compression standard. The video encoder then translates (more generally "transforms") the received coded bitstream into uncoded video information that may be displayed, stored, or otherwise handled.

Both video encoders and video decoders may be implemented using hardware and/or software configuration, including combinations of both hardware and software. Implementations of either or both may include the use of programmable hardware components such as general purpose central processing units CPUs, such as those found in personal computers (PCs), embedded processors, graphic card processors, digital signal processors (DSPs), field programmable gate arrays (FPGAs), or others. To implement at least parts of the video encoding or decoding, instructions may be needed, and those instructions may be stored and distributed using one or more non-transitory computer readable media. Computer readable media choices include compact disc read-only memory (CD-ROM), digital videodisc read-only memory (DVD-ROM), memory stick, embedded ROM, or others.

In the following, certain systems, methods and/or aspects relating in at least one broad aspect to video compression and decompression, i.e., the operations performed in a video encoder and/or decoder, will be described. A video decoder may perform all, or a subset of, the inverse operations of the encoding operations. Unless otherwise noted, techniques of video encoding described herein are intended also to encompass the inverse of the described video encoding techniques (namely associated video decoding).

The uncompressed, digital representation of video can be viewed as a sample stream, wherein the samples can be processed by the video display in scan order. One type of boundary often occurring in this sample stream is the boundary between pictures in the sample stream. Many video compression standards recognize this boundary and often divide the coded bitstream at these boundaries, for example through the insertion of a picture header or other metadata at the beginning of each uncoded picture.

For some applications, it may be advantageous to segment the coded picture into smaller data blocks, which segmenting can occur prior to, or during, the encoding. Two use cases for which picture segmentation may be advantageous are described below.

The first such use case involves parallel processing. Previously, standard definition video (e.g., 720×480 or 720×576 pixels) was the largest format in widespread commercial use. More recently HD (up to 1920×1080 pixels) formats as well as 4 k (4096×2048 pixels), 8 k (8192×4096 pixels), and still larger formats are emerging and finding use in a variety of application spaces. Despite the increase in affordable computing power over the years, as a result of the very large picture sizes associated with some of these newer and larger formats, it is often advantageous to leverage the efficiency of parallel processing to the encoding and decoding processes. Parallel encoding and decoding may occur at the instruction level (e.g., using SIMD), in a pipeline where several video coding units may be processed at different stages simultaneously, or on a large structure basis where collections of video coding sub units are processed by separate computing engines as separate entities (e.g., a multi-core general purpose processor). The last form of parallel processing requires picture segmentation.

The second such use case involves picture segmentation so as to create a bitstream suitable for efficient transport over packet networks. Codecs whose coded video is transported over IP or other packet network protocols can be subject to a maximum transmission unit ("MTU") size constraint. It is sometimes advantageous for the coded slice size to be such that the resulting packet containing the coded slice is as close to the MTU size as possible without exceeding that size, so as to keep the payload/packetization overhead ratio high, while avoiding fragmentation (and the resulting higher loss probability) by the network.

The MTU size differs widely from network to network. For example, the MTU size of many Internet connections may be set by the smallest MTU size of network infrastructure commonly used on the Internet, which often corresponds to limitations in Ethernet and may be roughly 1500 bytes.

The number of bits in a coded picture depends on many factors such as the source picture's dimensions, the desired quality, the complexity of the content in terms of suitability for prediction, the coding efficiency of the video coding standard, and other factors. However, even at moderate quality settings and content complexity, for sequences of HD resolution and above, the size of an average coded picture easily exceeds the MTU size. For example, a video conferencing encoder can require about 2 Mbits/sec to encode a 720 p60 video sequence. This results in an average coded picture size of roughly 33000 bits or 4125 bytes, which is considerably more than the approximately 1500 bytes of the Internet's MTU size. At higher resolutions, the average picture size increases to values significantly above the Internet's MTU size. Assuming a similar compression ratio as in the 720 p60 example above, a 4096×2048 (4 k) video at 60 fps (4 kp60) may require over 300,000 bits, or 25 MTU-sized packets for each coded video picture.

In many video coding standards, a picture segment (or, at least, one form of a picture segment) is known as a "slice". In the following description, any kind of (e.g., video coding standard based) coded picture fragmentation that breaks any form of in-picture prediction or other coding mechanism may be referred to generally as a "slice". As such, structures such as the Group Of Blocks ("GOB") in ITU.T Rec. H.261 or ITU Rec. H.263 (available from the ITU; see above for H.264), slices in H.264 or the MPEG family of standards, may each constitute a "slice" as this term is used herein throughout. However, fragmentation units of RFC3984 or data partitions of H.264 may not constitute a "slice", as this term is used herein throughout, even if they subdivide the bitstream of a coded picture into smaller datablocks, because they do not break in picture prediction or another coding mechanism.

One advantage of using slices over media unaware segmentation mechanisms, such as, for example, those provided by IP at the routing layer, is that slices are at least to a certain extent independently decodeable (as discussed below in more detail). The loss of one slice therefore does not necessarily render the other slices of a coded picture unusable or un-decodeable. Depending on the implementation of a fragmentation mechanism, the loss of a fragment, in contrast, may well render many other fragments unusable.

Many or all in-picture prediction mechanisms or coding mechanisms may broken by the decoding of a picture header (or equivalent). Whether those prediction mechanisms are broken also by the detection of a slice header may depend on the video compression standard, and the type of slice in use.

In H.264, individual video pictures may be segmented into one or more slices, thereby accommodating applications requiring or otherwise utilized pictures that are partitioned as part of the encoding/decoding process. Slices in H.264 may be independently decodeable with respect to motion vector prediction, intra prediction, CA-VLC and CABAC states, and other aspects of the H.264 standard. While this decoding independence may realize increases in error resilience, disallowing the aforementioned prediction across slice boundaries may tend to reduce coding efficiency.

In H.263, a video encoder has more flexibility in selecting which prediction mechanisms are broken through the use of slices or GOBs with non-empty GOB headers. For example, there is a bit included in the picture header, selectable when Annex R is in use, which signals to the decoder that no prediction at all occurs across slice/GOB boundaries. If the bit is not set, though, motion vectors may point outside of the current slice, thereby potentially "importing" sample values that are used for motion compensation within the current slice. Further, loop filtering may incorporate sample values outside of the slice.

In most or all existing video coding standards, with the possible exception of flexible macroblock ordering ("FMO") used as part of H.264, macroblocks within slices are ordered in raster scan order. Consequently, when video sequences with large picture sizes are partitioned into slices that encompass only a relatively small percentage of all macroblocks in the picture, the slices tend to be elongated when viewed spatially.

FIG. 1 shows an example picture 100 which is broken into slices in accordance with the prior art. Example picture 100 has a matrix 101 of 6×4 macroblocks, their boundaries indicated through hairlines. The picture 100 is divided into two slices 102, 103, with slice boundary 104 between the two slices 102, 103 indicated by a bold line. The first slice 102 contains 10 macroblocks in scan order, specifically, macroblock 1 through 10. The second slice 103 contains the remaining 14 macroblocks in the matrix 101 (i.e., macroblocks 11 through 24). The numerals in the macroblocks (e.g., numeral '11' in macroblock 105) are the addresses of the macroblocks according to scan order.

The bitstream 106 represents the coded picture corresponding to picture 100, and can include one or more parameter sets 107 as an example of a high level syntax structure, which can include syntax elements relevant to more than one of the coded slices of the picture 100. The parameter set(s) 107 can be followed by one or more slices, each such slice comprising a corresponding slice header 108, 110, and corresponding slice data 109, 111, respectively. Accordingly, in this example, slice header 108 may be associated with slice data 109 and may correspond to slice 102 in matrix 101, while slice header 110 may be associated with slice data 111 and may corresponding to slice 103. The slice headers 108, 110 may include information such as the address of the first macroblock of that respective slice, according to scan order. For example, the second slice 103 when coded into bitstream 106 starts with slice header 110 that includes a first macroblock address of '11', which designates the address of macroblock 105.

As can be seen in FIG. 1, slices 102 and 103 are somewhat elongated in the sense that each of slices 102 and 103 span more macroblocks horizontally (i.e., 6 macroblocks) than vertically (i.e., 2 to 3 macroblocks). Elongated slices such as slices 102 and 103 tend to contain diverse picture content as a result of the large distance from end to end horizontally.

Further, elongated slices tend to have low ratios of slice area to slice perimeter/boundary. The combination of slices containing diverse picture content with relatively low area to perimeter/boundary ratios can be disadvantageous from a coding efficiency perspective when compared with a slice that encompasses a more squared area of a picture, such as squares or other geometric figures close to a square. Slices with this geometric property may henceforth be called "compact" slices within this description.

Also, many entropy coding tools that have two-dimensional properties, such as the coding of motion vectors or intra prediction modes, may be optimized for squared picture aspect ratios. For example, in H.264, the coding of a horizontal motion vector of a given length costs roughly the same number of bits as the coding of a vertical motion vector of the same length. Consequently, these coding tools may yield a better compression for compact slices than for "elongated" slices, such as slices 102 and 103 shown in FIG. 1.

Improved coding efficiency for compact slices may further arise from the fact homogenous content, which is more likely to be found in a compact slice, may be more efficiently encoded as compared with the relatively diverse content that is more likely to be found in an elongated slice. As a general though not necessarily absolute rule, picture content is more likely to be homogenous in a compact slice because the spatial distance from the center to the boundaries of the slice is less, on average, for a compact slice than for an elongated slice. Further, having a higher slice area to slice boundary ratio for compact slices means that fewer prediction mechanisms may generally be broken in a given picture, thereby resulting in higher coding efficiency.

In H.264, FMO allows the video encoder to effectively produce rectangular slices by defining rectangular slice groups. FMO is a highly generalized coding tool that was designed to address several issues encountered in video coding. However, from a practical standpoint, FMO tends to be perceived as having a relatively high degree of implementation complexity, resulting in somewhat limited adoption as an aspect of standard video compression. A simpler coding tool that may realize improved coding efficiency, as well as parallel encoding and decoding, may address or ameliorate one or more of the complexity issues associated with a full FMO implementation.

The issue of elongated slices may also appear in an extreme case in many MPEG-2 based encoding schemes. For example, in MPEG-2 encoding, it is often the case that each single row of macroblocks within a picture is encoded into a slice, thereby effectively breaking any in picture prediction mechanisms in the vertical dimension within the picture.

Rectangular slice mode is one of two sub-modes specified in Annex K of H.263, another being "scan order slice mode", which has properties similar to the slices of H.264 discussed above. Rectangular slices as provided for in H.263 may offer one or more of the earlier described advantages that compact slices provide. However, H.263 requires that the dimensions (specifically the width) of each slice must be conveyed in its corresponding header, which leads to coding inefficiency, for example, in applications in which the slice sizes in the horizontal dimension do not change from picture to picture. In addition, Annex K of H.263 does not specify a minimum slice width that would effectively prevent vertically elongated slices from being used. Vertically elongated slices may introduce implementation difficulties and would not in every case provide the desired coding efficiency advantages that, for the reasons discussed above for horizontally elongated slices, may be provided through use of more compact slices.

Constraining the slice to have a rectangular shape can also be disadvantageous in certain cases. First, rectangular slices may perform sub-optimally in applications for which the bitstreams use transport protocols subject to an MTU. For example, packets may be fragmented if the number of bits within a give packet exceeds the MTU limit imposed on the bitstream, which can be undesirable from at least network performance and error resilience perspectives. Conversely, if the number of bits within a given packet is far below the MTU limit, then the ratio of the number of bits in the transport and slice headers becomes relatively large as compared with the number of bits in the packet payload, thereby leading to coding inefficiencies. Requiring slices to be rectangular in shape limits the encoder's ability to precisely control the number of bits in the coded slice so as to avoid the above-mentioned disadvantages.

Second, rectangular slices may perform sub-optimally in applications that utilize parallel encoding and/or decoding. When encoding and/or decoding in parallel, it is typically advantageous to partition a picture into different parts such that each part of the picture requires approximately the same amount of computational power to encode. By partitioning the picture in this way, each part of the picture may therefore be encoded with nearly the same latency to thereby reduce or minimize lag between the encoding times of different parts of the picture. An encoder constrained to use rectangular slices may not be able to precisely control the amount of CPU capacity required to encode and/or decode each slice and thereby avoid this potential disadvantage.

In order to facilitate parallel decoding of slices belonging to the same coded picture, a decoder will generally assign coded picture segments to the various processors, processor cores, or other independently operating decoding mechanisms made available to the decoder for parallel decoding. Without the use of FMO, this was a generally difficult, in some cases extremely difficult, task for previous video coding standards to handle, as those previous standards would allow too much flexibility in the bit stream generation. For example, in H.264, it is possible that one picture may be coded in a single slice and another picture into dozens of slices within the same bitstream. If parallelization occurs at the slice level, when a picture is coded in a single slice, the processor assigned to decode that picture will need to be provisioned to handle its decoding in full. As a result, without imposing restrictions outside of the video coding standard, there may be comparatively little advantage realized by building parallel decoders if each decoding processor will need to be provisioned to be capable of handling a whole picture in any event.

The slice coding used in many MPEG-2 encoders is widely viewed to be the result of an agreement to utilize an informal Cable Labs specification that suggested a one slice per macroblock row segmentation scheme. Widespread acceptance of this informal specification was eventually gained. While there may have been value in such a segmentation scheme when the first MPEG-2 products became available, around 1995, today the various restrictions associated with the historical specification may significantly limit coding efficiency, although parallelization of decoding of (at least SD-coded) pictures has been a relative non-issue for at least a decade.

A need therefore exists for an improved method and system for picture segmentation that addresses, ameliorates or otherwise provides a useful alternative to the existing shortcomings of video encoders both in terms of MTU size matching and parallel decoding. Accordingly, a solution that addresses, at least in part, the above and other shortcomings is desired.

SUMMARY

Embodiments of the invention relate in one or more broad aspects to techniques for segmenting a coded picture into columns and slices.

In some embodiments, a plurality of columns may be defined in one or more syntax elements placed in one or more high level syntax structures, such as slice headers or parameter sets. The columns so defined may be of any width between, for example, one Coded Tree Block (CTB, as defined in, for example in WD4: (B. Bross et. al., "WD4: Working Draft 4 of High-Efficiency Video Coding", available from http://wftp3.itu.int/av-arch/jctvc-site/2011_07_F_Torino/) and the entire horizontal size of the picture as measured in CTBs.

In some embodiments, a column boundary between adjacent columns may break one or more prediction mechanism or loop filtering mechanisms of the video codec. The prediction or loop filter mechanisms broken by column boundaries may be the same or different from those broken by slice boundaries.

In some embodiments, the granularity for calculating and specifying column width can be a Largest Coding Unit (LCU), and a coded tree block (CTB) may be of the same size as an LCU.

In some embodiments, N columns may be defined by a syntax element N that indicates the number of columns in a picture, and which may be followed by N−1 syntax elements that indicate the corresponding widths of each of the N columns. The width of a designated column, for example the right-most column, may be computed, for example, by subtracting the sum of the widths of the left-most N−1 columns from the width of the picture.

In some embodiments, each column in the picture may have an equal width (except perhaps for one pre-defined column, such as the rightmost column, which can be of lesser width) and a syntax element W may be used to indicate such equal width of every column (except the one pre-defined column. The syntax element W may be placed, for example, in a high level syntax element structure such as a parameter set. In such cases, the width of the one pre-defined column can be determined based on a division operation involving W and the width of the picture, represented by N, whereby the width of the one pre-defined column may be taken as the remainder when N is divided by W.

In some embodiments, each column in the picture may have an equal width (except perhaps for one pre-defined column, such as the rightmost column, which can be of lesser width, in case the width of a picture in CTBs is not an integer divisible of N.), and a syntax element N may be used to indicate the number of equally wide columns (exclusive perhaps of the one pre-defined column). In such cases, the width of all N columns may be determined by dividing the width of the picture in CTBs by N, with the width of the pre-defined column then equalling the remainder of the division operation.

In some embodiments, a syntax element N may be used to indicate the number of columns in a picture. The equal column width W, in units of LCUs, equals the width of the picture, in units of LCUs, divided by N.

In some embodiments, if the picture width is not an integer divisible by the equal column width W, then one pre-defined column, for example the rightmost column, may have a width that is the remainder of a division operation between the width of the picture (measured, for example, in CTBs) and W−1.

In some embodiments, a slice may encompass one or more CTBs each located within a single column, thereby enabling MTU size matching, while still allowing for parallelization through columns.

In some embodiments, a slice may encompass CTBs that are located in more than one column.

In some embodiments, the width of a column may be adjusted in a slice header or comparable syntax structure, thereby allowing to "load balance" the computational resources in the encoder. Such adjustment of column width may be advantageous if the content complexity is different in different horizontal areas in a source picture sequence.

In some embodiments, a high level syntax element may be used to fix the size of all columns of a picture, thereby allowing an efficient assignment of each column to a single processor or equivalent in a parallel encoding or decoding scenario.

In some embodiments, a constraint for the minimum and/or maximum horizontal width of a column may be imposed. Such constraint may in some cases aid parallelization and can improve coding efficiency. The constraint may, for example, be codified in the level specification of a standard, or in a high level syntax element, or can be adapted by optimizing a function that can involve MTU size and average bits per CTB (which can be derived from bitrate, frame rate, and frame size in CTBs).

In some embodiments, a scan order of CTBs may be used for decoding and/or encoding, according to which CTBs may be processed in an ordered sequence, at a first level, by column from left-to-right across all columns in the picture, and a second level below the first level, by CTB from left-to-right and top-to-bottom across all CTBs within a given column.

In one broad aspect, there is provided a method for encoding a video picture comprising a plurality of coded tree blocks (CTBs) arranged into at least two rows and at least one column of CTBs. The method may involve encoding a corresponding column width of each at least one column, each column width greater than zero and a sum of all column widths equal to a horizontal dimension of the video picture, and encoding at least one slice of the video picture. In some cases, the at least one the slice may include at least two CTBs located in at least two rows of CTBs.

In another broad aspect, there is provided one or more non-transitory computer-readable media on which are stored instructions arranged to enable one or more processors to perform a method for video encoding a video picture comprising a plurality of coded tree blocks (CTBs) arranged into at least two rows and at least one column of CTBs. The method may include encoding a corresponding column width of each at least one column, each column width greater than zero and a sum of all column widths equal to a horizontal dimension of the video picture, and encoding at least one slice of the video picture. In some cases, the at least one slice may include at least two CTBs located in at least two rows of CTBs.

In some embodiments, according to either of the above two aspects, the method may further include breaking at least one form of prediction or in-loop filtering at column boundaries between adjacent columns of CTBs.

In some embodiments, according to either of the above two aspects, the method may further include encoding at least one of a number of columns, and a width of a column into a parameter set.

In some embodiments, according to either of the above two aspects, the corresponding column width of at least one column may be variable between at least two rows of CTBs in the video picture. In such embodiments, such variability may be controlled by coding the corresponding column width in a slice header.

In some embodiments, according to either of the above two aspects, the method may further include encoding the plurality of CTBs following a scan order of CTBs, according to which the plurality of CTBs are encoded sequentially by column from left-to-right across a plurality of columns, and sequentially by CTB from left-to-right and top-to-bottom within each of the plurality of columns.

In yet another broad aspect, there is provided a method for decoding a coded video picture comprising a plurality of coded tree blocks (CTBs) arranged into at least two rows and at least one column of CTBs. The method may include obtaining at least one of (i) a corresponding column width of each at least one column and (ii) a number of columns, deriving the corresponding column width of each at least one column (if not obtained from the coded video picture), and decoding at least one slice of the coded video picture. In some cases, the at least one slice may include at least two CTBs located in at least two rows of CTBs.

In yet another broad aspect, there is provided one or more non-transitory computer-readable media on which are stored instructions arranged to enable one or more processors to perform a method for video decoding a coded video picture comprising a plurality of coded tree blocks (CTBs) arranged into at least two rows and at least one column of CTBs. The method may include obtaining at least one of (i) a corresponding column width of each at least one column and (ii) a number of columns, deriving the corresponding column width of each at least one column (if not obtained from the coded video picture), and decoding at least one slice of the coded video picture. In some cases, the at least one slice may include at least two CTBs located in at least two rows of CTBs.

In some embodiments, according to either of the above two aspects, the method may further include breaking at least one form of prediction or in-loop filtering at column boundaries between adjacent columns of CTBs.

In some embodiments, according to either of the above two aspects, at least one of the corresponding column width of the at least one column and the number of columns may be obtained from a parameter set.

In some embodiments, according to either of the above two aspects, the corresponding column width of at least one column may be variable between at least two rows of CTBs in the coded video picture. In such embodiments, such variability may be controlled by coding a column width in a slice header.

In some embodiments, according to either of the above two aspects, the method may further include decoding the plurality of CTBS following a scan order of CTBs, according to which the plurality of CTBs are decoded sequentially by column from left-to-right across a plurality of columns, and sequentially by CTB from left-to-right and top-to-bottom within each of the plurality of columns.

In yet another broad aspect, there is provided a video decoder for a coded video picture comprising a plurality of coded tree blocks (CTBs) arranged into at least two rows and at least one column of CTBs. The video decoder may include a plurality of column decoders, with each column decoder configured to decode slices of the coded video picture located within at least one column of CTBs allocated to that column decoder.

In some embodiments, according to the above aspect, each slice may be fully located within exactly one column.

In some embodiments, according to the above aspect, each column decoder may be a process running on at least one of a core of a multicore processor, or a multiprocessor.

In accordance with further aspects of the described embodiments, there is provided an apparatus such as a data processing system, a method for adapting such apparatus, as well as articles of manufacture such as a non-transitory computer readable medium or product having program instructions recorded thereon for practising the described method(s).

BRIEF DESCRIPTION OF THE DRAWINGS

Various features and advantages of the embodiments of the present invention will become apparent from the following detailed description, taken in combination with the appended drawings, in which:

FIG. 5 is a diagram illustrating the modification of column width in accordance with an embodiment of the invention;

It will be noted that throughout the appended drawings, like features are identified by like reference numerals.

DETAILED DESCRIPTION OF EMBODIMENTS

In the following description, details are set forth to provide an understanding of the invention. In some instances, certain software, circuits, structures and methods have not been described or shown in detail in order not to obscure the invention. The term "data processing system" is used herein to refer to any machine for processing data, including the computer systems, wireless devices, and network arrangements described herein. Embodiments of the present invention may be implemented in any computer programming language provided that the operating system of the data processing system provides the facilities that may support the requirements of these embodiments. Embodiments of the present invention may also be implemented in hardware or in a combination of hardware and software.

Embodiments of the present invention relate to picture segmentation in video compression using columns and slices.

Figure 2:
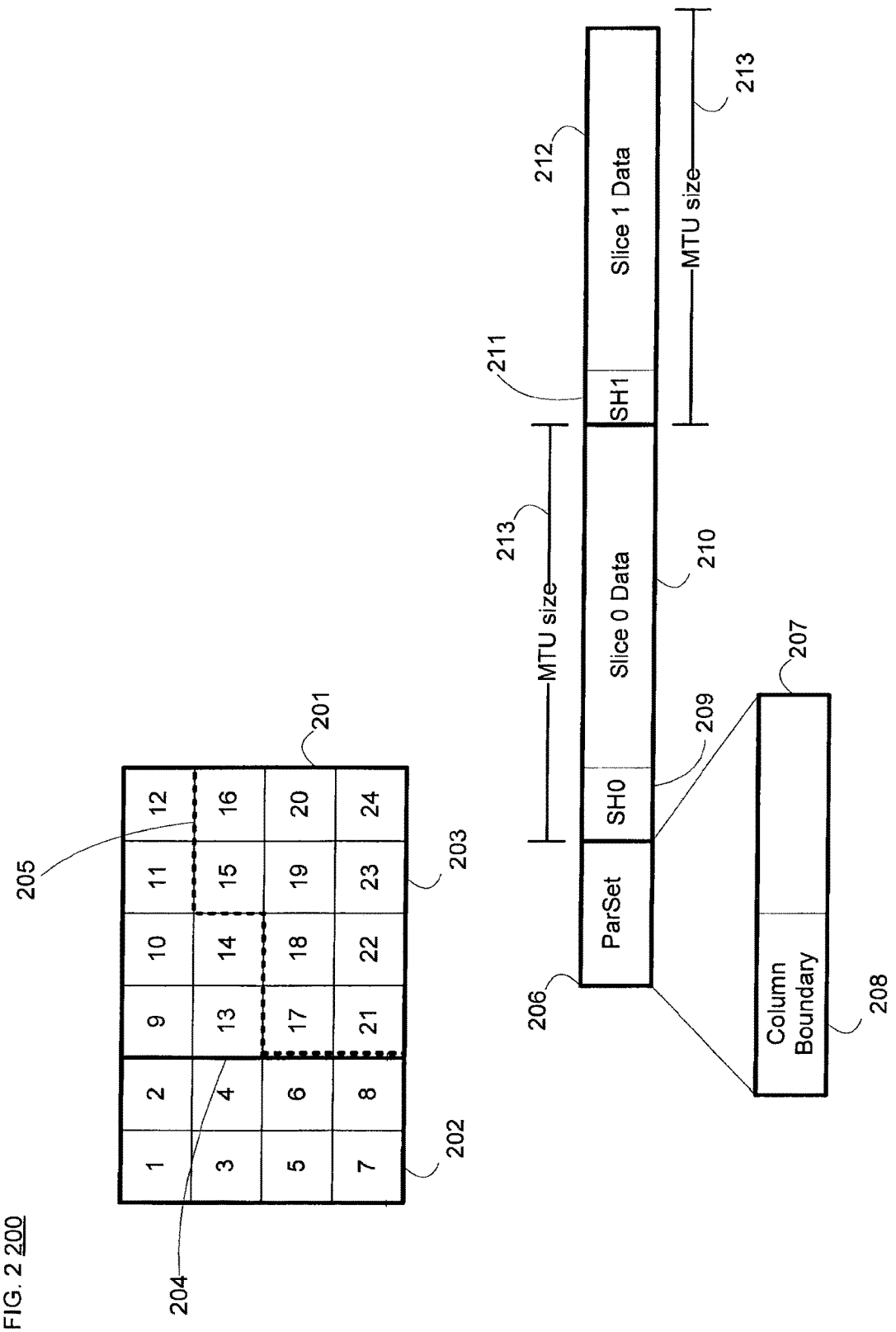
FIG. 2 is a diagram illustrating columns and slices in accordance with an embodiment of the invention.

Referring to FIG. 2, there is shown an exemplary segmentation 200 of a picture 201 in accordance with embodiments of the invention. The picture 201 is divided into a plurality of Coded Tree Blocks or macroblocks (henceforth referred to as "CTBs"). In this example, the picture 201 has dimensions of 6×4 CTBs. The boundaries of CTBs are shown generally as hairlines. The nature of the CTBs, and their specific dimensions, is variable and may be altered according to different embodiments. While the description below assumes that that CTBs included within picture 201 are square and of equal size (as it is common for macroblocks in H.264, for example), certain embodiments of the invention may not require such a property and can may be operable with CTBs of differing size(s), provided that in such embodiments it is possible to define one or more horizontal columns using those unevenly sized CTBs. For example, embodiments of the invention may be operable with macroblock pairs as used in H.264 interlace coding, or with the reduced resolution update mode of H.263. The embodiments may also be operable if there were CTBs of, for example, 32×32, 16×16, and 8×8 samples in the same picture.

Two columns 202, 203 are defined in the picture 201 and are shown divided by a column boundary depicted as boldface, solid line 204. The width of any column can be an integer multiple of the size of a CTB (or an integer multiple of the size of the smallest CTB possible) used within the picture 201. Columns may be of equal or unequal width within the picture 201. As shown, column 202 encompasses CTBs 1 through 8, and column 203 encompasses CTBs 9 through 24. Column 202 is two CTBs wide, whereas column 203 is four CTBs wide. However, the described embodiments are not limited to this number of columns nor to the exemplary column widths shown in FIG. 1.

Figure 1:
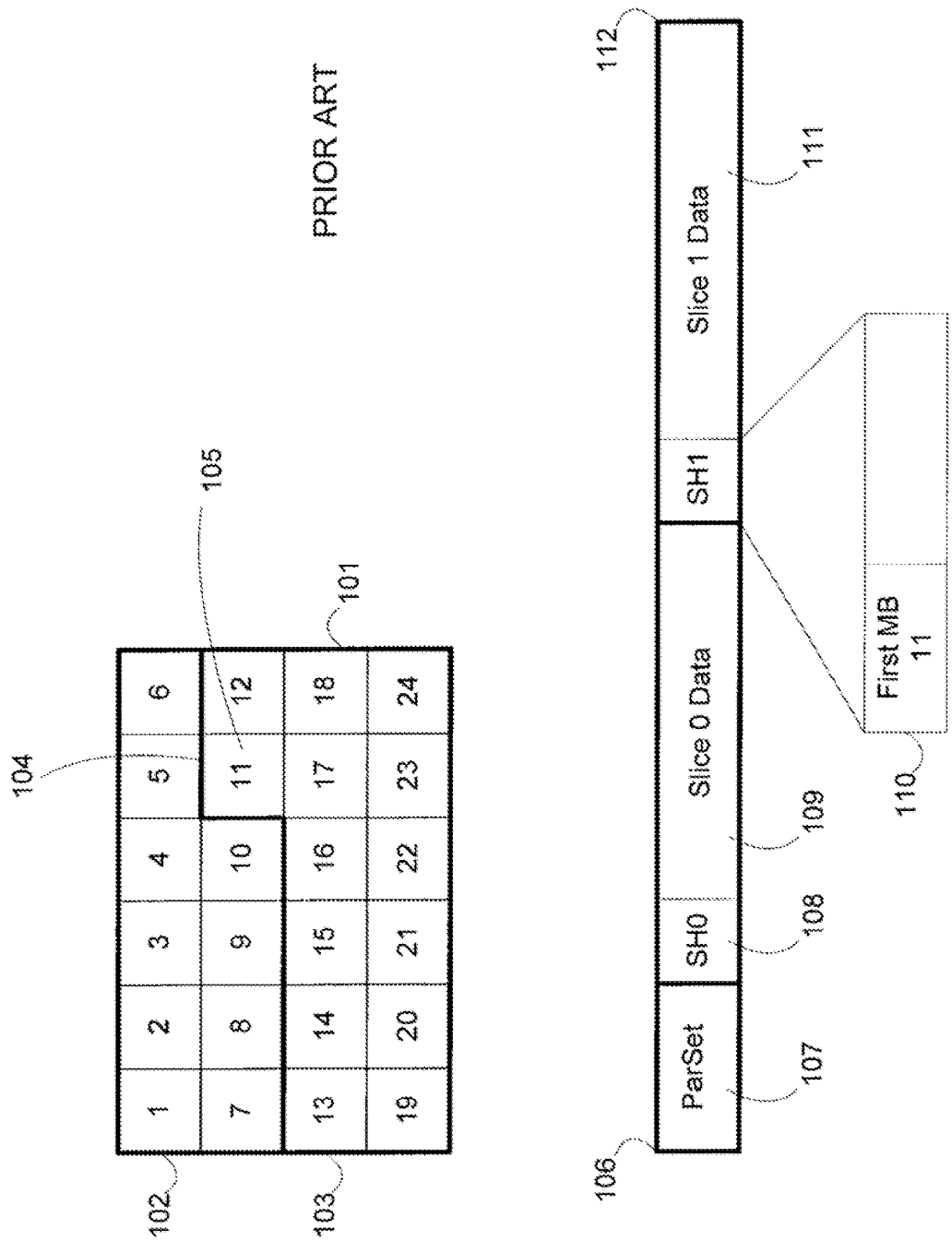
FIG. 1 is a diagram illustrating an exemplary picture having scan order slices and macroblocks addresses.

Shown also are two slices defined within picture 201 and delineated by the boldface punctuated bordering line 205. The first slice encompasses the CTBs with CTB addresses 1 through 14. The second slice encompasses CTBs with addresses 15 through 24. CTBs 1-8 of the first slice are located in column 202, whereas CTBs 9-14 of the first slice are located in column 203. Therefore, the first slice covers CTBs that are part of either column 202 and 203. The second slice includes CTBs 15-24, which are all located in column 203. Accordingly, the scan order of CTBs within picture 201 has changed from the per-picture scan order, as shown in FIG. 1, to a per-column scan order, as shown in FIG. 2. In accordance with the per-column scan order, the CTBs of column 202 are first enumerated in a column-local scan order (left-to-right, top-to-bottom throughout column 202), before the CTBs of column 203 are enumerated (by a column-local scan order defined in a similar way). If/where appropriate, the per-column scan order shown in FIG. 2 can be extended to pictures for which more than two columns have been defined.

The coded bitstream 206 represents the picture 201 and can contain a parameter set 207 (or can include a reference to a parameter set that has previously been decoded, as multiple pictures can refer to the same parameter set). The parameter set 207 can contain column boundary information 208, identifying directly or indirectly the width of one or more column(s), e.g., columns 202 and 203, as described later. Each of the coded slices can comprise a corresponding slice header 209, 211, and corresponding slice data 210, 212, respectively.

Picture segmentation with slices spanning column boundaries, as shown in FIG. 2, can provided one or more advantages, such as that the size of all coded slices (with the possible exception of the last slice of a given picture) can be adjusted to match the MTU size 213 as closely as possible, at least partly on account that coded slices may not include parts of coded CTBs. In the example of FIG. 2, the two coded slices (each comprising respective slice headers 209, 211 and slice data 210, 212) are shown as roughly of the same size so as to indicate that these coded slices carry roughly the same number of bits, which can be a number smaller, but close to, the MTU size 213. The MTU size 213 is shown as an interval, which, in this example, is constant for the two slices. While, in most cases, the MTU size 213 is a network property and constant for any packet, for the purpose of optimizing packet payload through the use of slices, other consideration(s) may urge adoption of a variable target size for coded slices. For example, for error resilience, it may be useful for some packets to carry redundant copies of parameter sets in addition to their slice payload. In such cases, the MTU size 213 may differ from packet to packet and, therefore, from coded slice to coded slice as well. The term "MTU size" is used in this broad sense throughout the description.

One advantage of allowing slices to span multiple columns across the boundaries between them is to allow for good MTU size matching. With slices able to span multiple columns, none of the slices will be artificially limited in size due to the presence of a column boundary. Another advantage can be that it is possible to represent the whole picture as a single slice (for example, where the MTU size is, in most cases, larger than the coded picture size), while still allowing for parallelization. For convenience, it may be assumed that a column boundary breaks all forms of prediction or in-loop filtering. Under this assumption, one example configuration of a parallel encoder may be as follows. Each processor/core of the parallel decoder may begin encoding the spatial area of a column, starting with the top-left CTB within the column and working sequentially in scan order to the bottom right macroblock, i.e., left-to-right and top-to-bottom. Assuming N columns in a picture and N processors/cores with the parallel decoder, this approach to encoding may results in N sub-bitstreams being generated, one from each processor/core. The N sub-bitstreams may then be combined to form a single bitstream representing the whole picture. A decoder receiving such bitstream may, from the parameter set (e.g., included in the bitstream), ascertain that it is being tasked for parallel decoding in N columns. The decoder may pre-process the combined bitstream by first decoding only syntax elements included in the bitstream (without also performing any computationally intensive reconstruction of CTBs) so as to identify the boundaries between the columns in the bitstream domain. As an example, one such boundary would be located between coded CTB 8 and coded CTB 9 of picture 201. Thereafter, the decoder may extract and/or copy the sub-bitstreams, broken up within the combined bitstream at the pre-identified boundaries, to the processors/cores for processing. The processors/cores within the decoder may independently reconstruct their assigned columns in the pixel domain, which may then be copied together to reconstruct the full image. Other possible implementation strategies are explained in more detail below.

One potential disadvantage of having slices spanning across column boundaries can arise because of difficulties in the implementation of parallelization, for example, when only a (small) subset of prediction and/or loop filtering mechanisms are broken by a column boundary. For example, if column 202 were to be decoded on a first processor, and column 203 were to be decoded on a second processor, then the state of the decoding engine (including information such as CABAC state, motion prediction state, and so on), or at least those parts of it which relate to prediction or loop filter tools not broken by column boundaries, would in at least some cases have to be handed over from the first processor to the second processor after the decoding of CTB 8, which in column-local scan order is the last macroblock in column 202. The implementation and computational complexity of this handover can depend on, for example, the prediction and loop filter tools that are disrupted by the presence of a column boundary. If, for example, a column boundary breaks any form of prediction but the prediction in the entropy coding, then only information pertaining to the entropy coding engine needs to be handed over. Co-pending U.S. patent application Ser. No. 13/336,475, filed even date herewith, entitled "METHOD AND SYSTEM FOR SELECTIVELY BREAKING PREDICTION IN VIDEO CODING", which is incorporated herein in its entirety, discloses, among other things, techniques to control the amount of data that needs to be handed over when a slice spans a column boundary.

Figure 3:
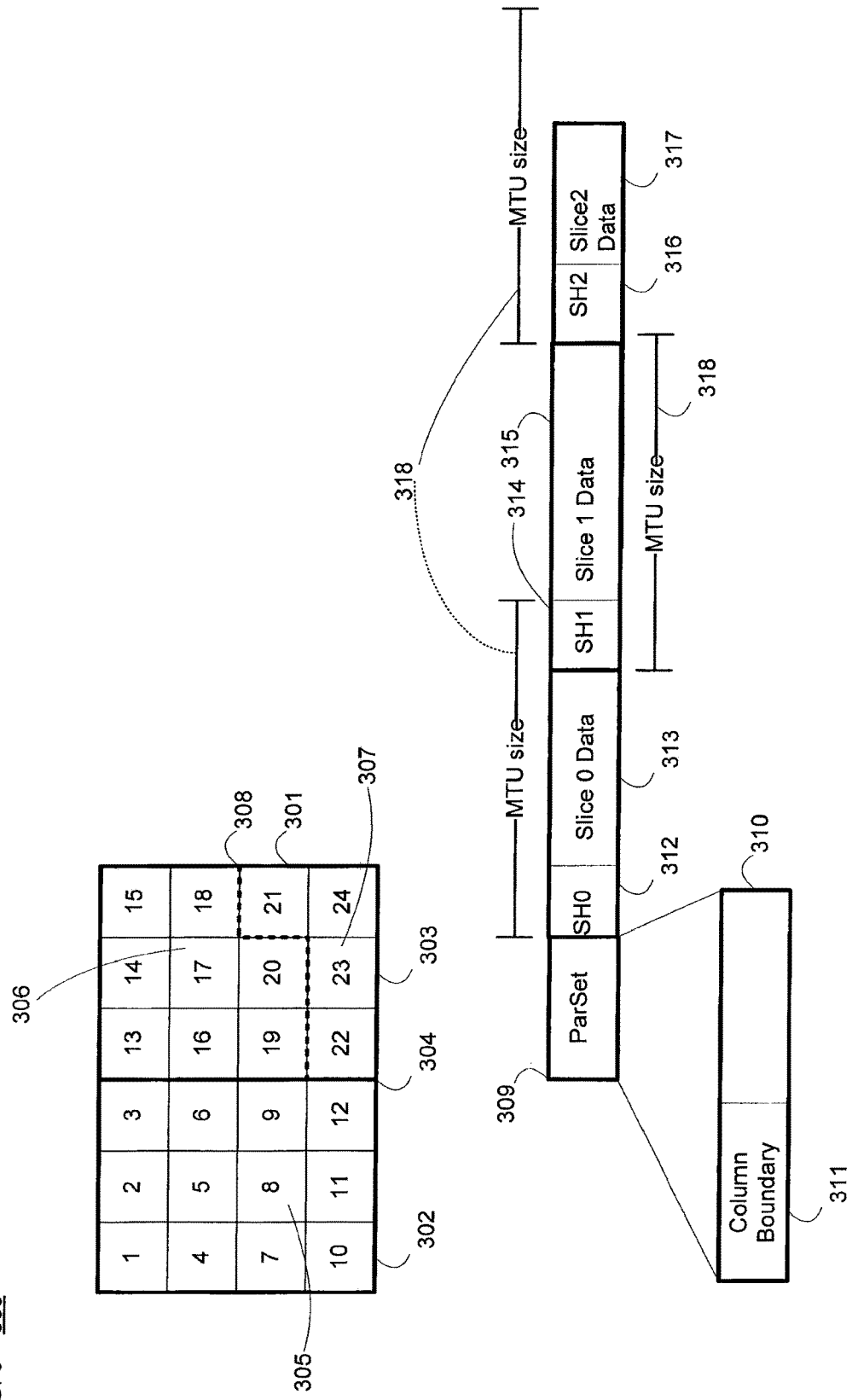
FIG. 3 is a diagram illustrating columns and slices (local to a given column) in accordance with an embodiment of the invention.

FIG. 3 illustrates the interaction between slices and columns of a video picture in a less general case 300, in particular, which is optimized for parallel processing of equally powerful processors (or other parallel processing entities such as processor cores), at the expense of the best possible MTU size matching. (Such optimization may also depend on the prediction and loop filtering tools that are broken through the use of columns; co-pending U.S. patent application Ser. No. 13/336,475, discloses, among other things, techniques to control the tools affected by column boundaries.)

As seen in FIG. 3, a picture 301 is divided in two columns 302, 303 of equal width (in this example, three CTBs wide), resulting in a similar number of CTBs to be assigned to each of columns 302, 303. Under the assumption that a given column is processed by a given processor or core, division of picture 301 into columns 302, 303 of equal widths also may result in roughly equal load for each processor or core. The column boundary 304 between the columns 302 and 303 is shown as a boldface line. All CTBs of column 302 are coded in a single slice 305. Whereas in column 303, two slices 306, 307 are defined and collectively include all of the CTBs of column 303, with each slice 306, 307 defined so as to stay within MTU size constraints. For example, slices 305, 306 and 307 may each satisfy MTU size constraints, despite containing a different number of macroblocks (twelve, eight, and four, respectively) where a higher average number of bits is required for the CTBs of column 303 relative to the CTBs of column 302, which can occur if/when one part of the picture 201 is more "complex" than the other. The slice boundary 308 between slices 306 and 307 within column 303 is indicated by a boldface, punctuated line. It should be noted that slices 305 and 306 are considerably more "compact" than would have been slices containing a similar number of CTBs but arranged in picture scan order. Therefore, the use of columns 302 and 303 may not only facilitate the use of parallel processing (as will be described in greater detail below), but also can aid in coding efficiency. Slice 307, in this example, while not being very compact as compared to slices 305 and 306 may still be more compact than it would have been without the use of columns 302 and 303. Once more, the scan order of CTBs is changed as previously described.

The coded bitstream 309 can contain a parameter set 310 comprising column boundary information 311. While the parameter set 309 may be shown in FIG. 3 to be adjacent to the coded slices of the coded picture, in various embodiments, it may be possible for the parameter set to be located elsewhere in the bitstream 309 or even in some cases to be conveyed out of band.

The coded picture contains three coded slices (i.e., slice 0, slice 1 and slice 2), each comprising a corresponding slice header 312, 314, 316, and corresponding slice data 313, 315, 317, respectively. The coded slice 0 includes coded slice header 312 and coded slice data 313, which includes the coded information of slice 305, and is depicted having a size (in coded bits) somewhere below the MTU size 318. Coded slice 1 includes coded slice header 314 and coded slice data 315 (corresponding to slice 306). In this example, when coding slice 1, the encoder is able to fill the packet almost up to MTU size 318 with slice header 314 and slice data 315. Note that it may not always be possible to fill the packet up to the last bit of the MTU size 318 because it is not possible to fragment a CTB into more than one slice. Accordingly, subject to this restriction, there may be extra bits leftover after encoding of the last CTB within the slice. Finally, slice 2 includes slice header 316 and slice data 317 (corresponding to slice 307), and is considerably smaller than the MTU size 318 because there are fewer CTBs to be coded in this slice, e.g., as compared to slice 0 and slice 1.

A static width of the columns within a picture can be specified at the sequence level (e.g., in a sequence parameter set), at the picture level (e.g., in a picture parameter set), or in other data structures in the bitstream covering at least one coded picture. Specifying column boundaries once for all slices in a sequence or picture has advantages for applications whose slices do not vary in width from picture to picture, in that the overhead associated with specifying a different slice structure is not required for every picture. It further has the advantage of efficiently allowing the distribution of coded bits among multiple processors or equivalent in a parallel decoding scenario. Dynamic column width adjustments are described later.

Column boundaries may be specified using one or more different data structures, parameters, rules, flags, or other suitable syntax. Using the sequence parameter set (SPS) as the exemplary high level syntax structure to convey column boundaries, the SPS can for example include:

(1) a variable N by which is coded the number of columns per picture. In such cases, if/when necessary and/or appropriate, the width of each column (in units of CTBs) may be derived by dividing the width of a picture (in units of CTBs) by N, if the width of the picture is divisible by N. Otherwise, the width of N−1 columns may be calculated by dividing the width of the picture by N−1, whereby the width of the final column (for example the rightmost column in the picture) would then be the remainder of the division operation.

(2) a variable W by which is coded the maximum width (in units of CTBs) of a column. In such cases, let N be width of the picture divided by W. Then the width of the first N columns is equal to W, and the width of the final column would be the remainder of the division operation.

(3) a variable N containing the number of columns, and a field of integers N−1 long containing values to represent the widths of each such column. This option allows for non-uniform column width as shown in FIG. 2.

Still other representations of column boundary information which are suitable for different applications may be apparent after familiarization with the present disclosure and are intended to be covered within the scope of the described embodiments.

A video coding standard can advantageously set limits for minimum or maximum column width that can occur in a bitstream. The limits can be specified, for example, in profile and level specifications. For example, a profile designed for high level parallel processing in case of high resolution video decoding, can require that columns must be used with a width no larger than, for example, 1920 samples (a 1080 p resolution, which is commonly decodeable in a single core, has a resolution of 1920 horizontal samples). On the other hand, the profile can require, for example, a minimum column width of no less than 640 samples. The lower limit can help to avoid worst-case scenarios and "elongated" slices in the Y dimension. The upper limit can be useful for a number of different reasons. First, as already described, coding efficiency can be improved due to fewer and less elongated slices. Second, the decoder can be based on sub-picture decoders each capable of decoding a single column (henceforth called "column decoders"), but not necessarily capable of handling a full picture. Third, memory requirements in the column decoders can be reduced as line buffers do not need to span the full picture width, but only the column width (plus perhaps implementation dependent padding). Other advantages of such an upper limit on column width may also be apparent.

Described next is the operation of a decoder on a bitstream containing slices and columns, noting how such operation may differ from the decoding process of a bitstream that has been generated without use of columns. For convenience, in the following description it will be assumed that coding of column width was performed according to option (3) above. However, the description should not be understood as being limited only to this type of coding and will apply also to the other two options described above, if/where necessary, by making suitable modification and/or alteration to the description.

In modern video coding standards, parameters pertaining to more than one slice can be stored in higher level syntax structures known as parameter sets. In older standards, these parameters can be stored in headers such as the picture, GOP, or sequence headers. To facilitate the following description, parameter sets are assumed henceforth, although embodiments of the invention may equally utilize other forms of high level syntax structures.

Figure 4:
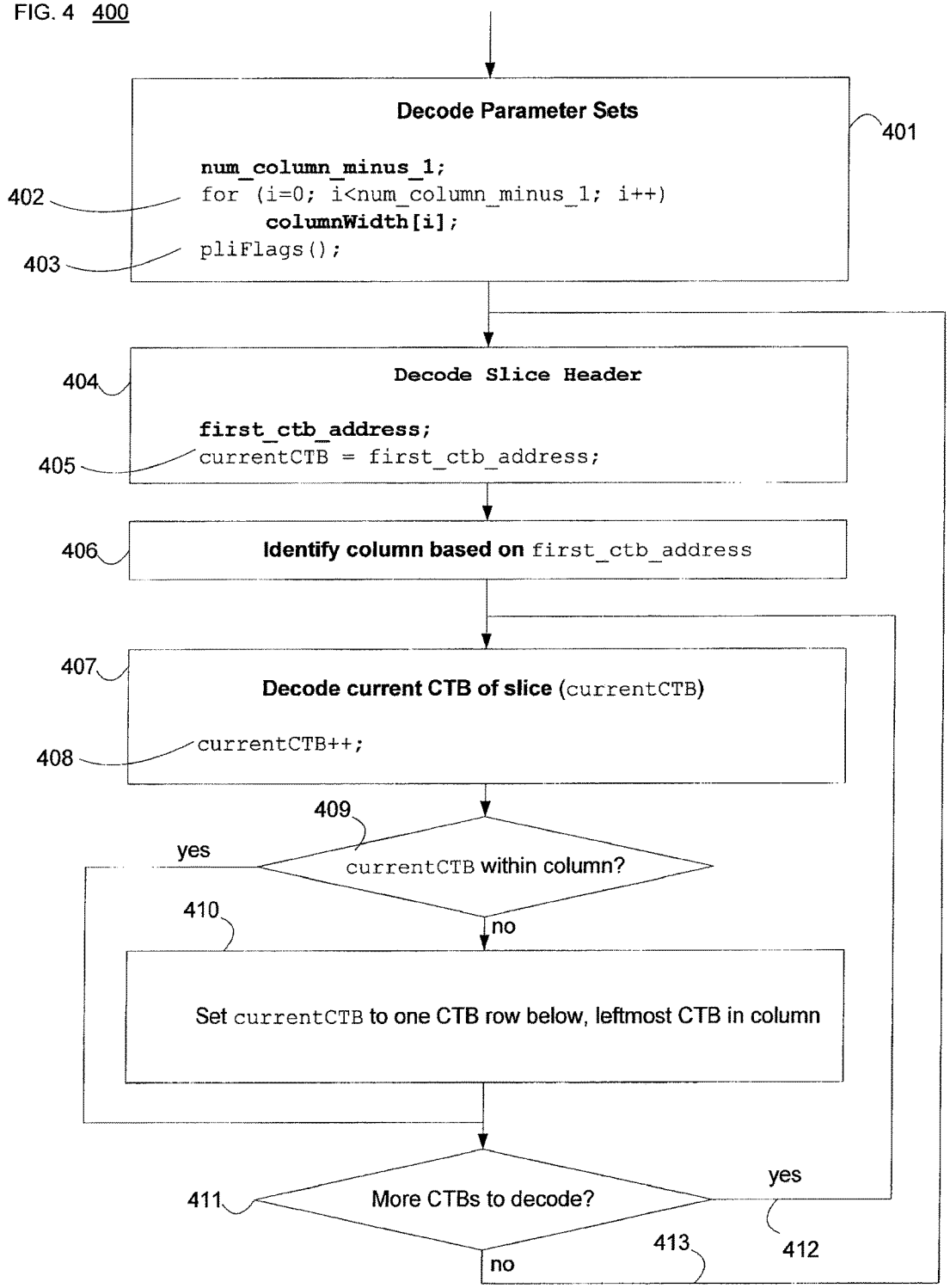
FIG. 4 is a flow diagram illustrating the operation of an exemplary decoder in accordance with an embodiment of the invention.

FIG. 4 shows a method 400 that illustrates the operation of an exemplary decoder in accordance with embodiments of the invention. First, so as to be able to decode slice data, one or more parameter sets may be decoded (401) as parameters stored in the parameter sets and which may be accessed through a reference stored in the slice header. In some embodiments, the parameter sets can contain information pertaining to, and which is sufficient to completely define, the column mechanism used within the pictures to be decoded. For example, the parameter sets may include parameters used to indicate the number of columns (i.e., "num_column_minus_1" in FIG. 4), and the width of each such column exclusive of the last column (i.e., "columnWidth[ ]" in FIG. 4). The width of the last column in the coded picture can equal the distance between the rightmost column boundary and the right hand picture boundary.

The stored parameters (e.g., "num_column_minus_1" and "columnWidth[ ]") may be decoded (402) as one part of the parameter set decoding (401). The decoding (402) may be a sub-step of the decoding (401) and may be performed at any appropriate time during the parameter set decoding (401). The exact order may, for example, be constrained by the syntax of the parameter sets themselves (which can mandate the location of the information decoded in 402 relative to other entries in the parameter set).

During the parameter set decoding (401), information relating to the prediction and/or in-loop filtering tools can also be decoded, as described further in co-pending U.S. patent application Ser. No. 13/336,475. Decoding of information relating to prediction and/or in-loop filtering tools is indicated generally in FIG. 4 at 403, and may also be considered to be one part of the parameter set decoding (401).

Following the decoding (401) of parameter set information in method 400, slice decoding and reconstruction can commence.

First, a slice header can be decoded (404). In the slice header, information can be available that allows for the decoder to associate the given slice with the column in which that given slice is included. For example, the slice header can contain a CTB address (i.e., as indicated by "first_ctb_address" in FIG. 4) that represents the address of the first CTB included within the slice. The encoded CTB address may be decoded (405) and used as the initial value for a parameter used by the decoder to keep track of the current CTB address (i.e., "currentCTB" in FIG. 4) during the decoding process. Then, the column in which the slice resides can be identified (406) based on the address of the first CTB included within the slice by associating that first CTB with a particular column defined in the coded picture.

For example, referring back to FIG. 1, CTB addresses (of which the CTB address decoded at 405 is one instance) may be entropy coded representations of the locations of each given CTB in the picture, in scan order, as indicated by numerals of FIG. 1 centred in the CTBs. To associate slices with columns, the horizontal component of the CTB address of the first CTB in the given slice can be compared to the column boundaries, defined for the coded picture, which may be derived from column width information obtained during the decoding of the parameter sets (and may possibly be modified during later slice decoding, as outlined below). In some embodiments of the invention, where each given slice may be constrained to resides in its entirety within a given column, slices may be associated with columns by identifying the column in which the first CTB within that given slice resides (because, by definition, all remaining CTBs in the slice would be located within the same column). This identification can be undertaken according to block 611 and 612 of FIG. 6, which are discussed in more detail below.

Referring again to FIG. 4, the first (initial) column for the slice to be decoded is identified (406). The decoding of coded CTBs in the slice may then proceed as specified in one or more video compression standards for the decoding of CTBs to which the decoding may comply, which can include steps such as entropy decoding, motion compensation to form a predictor, inverse quantization and inverse transform of coefficients to calculate a residual, adding the residual to the motion compensated predictor, in-CTB deblock-filtering the resulting samples, and so forth, with the exception of the handling of CTB addresses and the use of data outside of the slice based on its availability for prediction. In the following, one example outlining one possible implementation strategy is outlined, although other strategies may be apparent as well after familiarization with the present disclosure.

First, the CTBs texture, motion, and other information can be decoded and the current CTB being handled by the decoder can be reconstructed (407), which can involve any or all of the different steps noted above in the context of CTB decoding, while also observing the availability of prediction information outside of the slice or column boundary.

Then, the current CTB address may be incremented (408). If the incremented CTB address is determined (409) to still be left of the column's right-hand boundary, no further updating of the CTB address is required (indicating in FIG. 4 by the arrow bypassing block 410 directly to block 411). However, if it is determined (409) that the incremented CTB address is outside the column (that is, equal or right of the column's right-hand boundary), then the CTB address is reset (410) to the address of the first CTB in the next line of CTBs within the column. In other words, the horizontal component of the CTB address is set to the leftmost CTB of the column (as indicated by the parameter "colBound[ ]" in FIG. 6), and the vertical component of the CTB address is increased by one.

If, after execution of blocks 408 to 410, the vertical component of the CTB address exceeds the vertical size of the picture, then the slice may span more than one column. In this case, the CTB address may be reset, for example, to the top-left CTB address in the column to the left of the previous column. Decoding and CTB address changes continue in this column.

At this point, it is determined (411) whether more data (indicating one or more CTBs) is available in the slice to be decoded. If it is determined (411) that more data remains in the slice to be decoded, then method 400 proceeds (412) back to block 407, and the decoding continues with the next CTB within the slice. However, if it is determined (411) that no data remains in the slice to be decoded, then method 400 proceeds (413) back to block 404, and the decoding continues with the next slice in the picture.

According to embodiments of the invention, a decoder can read (initial) column boundary information from high level structures such as picture or sequence parameter sets. For example, this can be implemented in a mechanism that parses first a syntax element (i.e., "num_column_minus_1") from the bitstream. This syntax element may advantageously be part of a picture (or higher) syntax structure, such as a picture parameter set, sequence parameter set, picture header, or comparable structure. If the value of "num_column_minus_1" is greater than 0, then it may be inferred that the number of column boundaries present in a conformant bitstream will be equal to the value stored in this parameter, and there num_column_minus_1 column widths may be parsed. The widths of the correspondingly parsed columns can be indicated in terms of CTBs. The syntax described above is specified in the style of the H.264 syntax specification, parts of which are summarized below for convenience.

Specifically, in the syntax description provided below, a boldface variable (i.e., lines 1 and 4 below), in comparison to a plain formatted line, may represent bits that are fetched from the bitstream as a side effect of or otherwise in conjunction with determining the value of the variable. Once read, the value can be used in the decoding process however the variable is no longer set in boldface, since the use of the variable is from that point onwards no longer associated with a bitstream fetch.

```
num_column_minus_1
if (num_column_minus_1 > 0) {
    for (i=0; i < num_column_minus_1; i++) {
        columnWidth[i]
    }
}
```

If column boundaries can be specified at more than one level, according to the given compression standard, then the syntax of column boundaries can be the same at various levels, for example, sequence and/or picture level. In this case, advantageously, column boundaries indicated at a lower relative level (i.e., the picture level) can take precedence over column boundaries indicated at a higher relative level (i.e., the sequence level).

The parsed columnWidth[ ] values may be used to derive the column boundaries as shown below:

```
if (num_column_minus_1 > 0) {
    columnBoundary[1] = columnWidth[0];
    for (i=1; i < num_column_minus_1; i++) {
        columnBoundary[i+1]=columnBoundary[i] + columnWidth[i];
    }
}
```

In the following, embodiments of the present invention in which the column boundaries can be adjusted during the coding of a picture, i.e., at the slice level are described.

Figure 5:
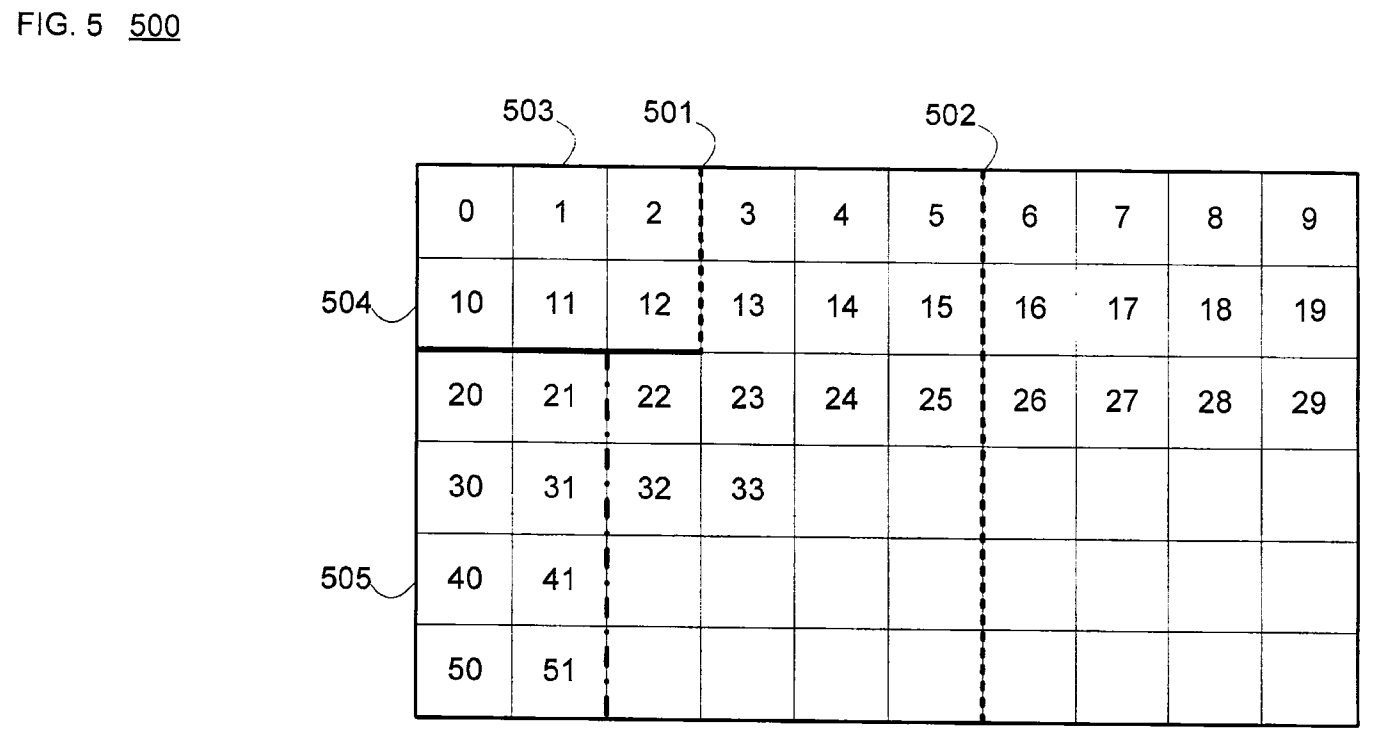

Referring to FIG. 5, there is shown a diagram illustrating the modification 500 of column width in accordance with embodiments of the invention. In FIG. 5, the location of column boundaries can be modified at the slice level (e.g., based on information from a slice header). The modification 500 may pertain only to the current picture and not to other pictures in the coded bitstream. When encoding processing parallelization is involved and columns may be processed by independent processors or similar units, the modification 500 may provide an advantage in that the number of CTBs per column can be adjusted to processor load possibly from outside load factors (other processes not related to the video encoding), content complexity (that may vary from column to column), or still other factors.

In the following description, for convenience, the slice header is used for conveying modification information because, in certain contexts, the slice header may be the most appropriate syntax structure in H.264 for such purpose. The use of the slice header for information pertaining to more than one slice is not necessarily in line with H.264's syntax model (for example, in H.264, all information that pertains to more than one slice should be included in parameter sets only), but is in line with some older video compression standards (for example, in H.261, GOB header information can be predicted from previous GOB headers, and GOBs are at least in some respects similar to equivalent to H.264 slices). At the same time, if a mechanism were to be included in newer video compression standards, which would allow the coding of properties at the slice level that pertains to more than just the current slice, then such syntax structure could in some cases be a more suitable location for the information presented below than in the slice header itself. For example, included in WD4 is an Adaptation Parameter Set (APS), which is designed to carry information that is likely to change from picture to picture (in contrast to the picture parameter set, which carries information that is unlikely to change from picture to picture). Also being considered in JCT-VC are proposals to allow "updating" an APS at slice boundaries, which, if accepted, would also make the APS an appropriate syntax structure for column width update information, as described below.

In some embodiments of the invention, the column boundaries that have been changed through the override mechanism discussed below revert back to the locations specified at the picture or sequence level when encoding/decoding of the current picture is complete. This feature may, at least partly, compensate for the architectural lack of cleanliness of using the slice header to code information pertaining to more than one slice. For example, one possible reason for disallowing the use of picture headers and similar data structures in H.264 is to avoid error propagation due to corrupted header structures. Reverting back to data conveyed in parameter sets (which have been designed to be very difficult to ever get corrupted) after each picture may ensure that header corruption is limited to one given picture, rather to all pictures following the picture in which the header corruption has occurred.

Shown in FIG. 5 are two original column boundaries 501 and 502, which are depicted as punctuated, boldface, vertical lines. In the example, it is assumed that the encoder wishes for some reason to reduce the column width of the leftmost column 503. The motivation of the encoder to make this adjustment is not generally limited and may include, for example, processor load balancing aspects, or relatively (with respect to other columns) high coding complexity of the content in the leftmost column, that would lead to more bits in the CTBs of this column, and, in consequence, results in elongated slices unless the column width is reduced.

According to the modification 500, column boundary 502 spans the entire vertical height of the picture, while column boundary 501 spans only a portion of the entire vertical height of the picture, i.e., the two uppermost rows of CTBs. The remainder of the column boundary is offset relative to column boundary 501 and, consequently, the leftmost column 503 has variable width. For example, column 503 may be split into two different slices of different width. As shown in FIG. 5, slice 504 within column 503 may have a first width, which is set by the original column boundary 501, whereas slice 505 within column 503 may have a second width different from the first width, and which is set by the offset column boundary according to the modification 500.

Column boundaries can be modified at the slice level by including boundary offset values to shift a column boundary to, for example, the left, if the offset value is negative, or alternatively to, for example, the right, if the offset value is positive. The slice header of the slice 505 in the leftmost column 503 may, for example, include information to the extent that the original column boundary 501 between the leftmost and middle columns, as defined with respect to slice 504, be shifted by one CTB to the left in respect of the slice 505. As a result, CTB 22 belongs now to the middle column (as opposed to the leftmost column 503), and coding continues in the leftmost column 503 with slice 505, which encompasses CTBs 20, 21, 30, 31, 40, 41, 50, and 51 in this particular example.

There are a number of corner cases that could potentially make implementation of the modification 500 described above seem unnecessarily complex and/or inefficient from a caching viewpoint. However, such corner cases may be effectively handled by a number of restrictions concerning the moving of column boundaries that can be imposed in various embodiments, and which are described further below.

During picture decoding, shifting of the column boundary may come into effect starting at the CTB line in which is locate the address of the first CTB of the slice to contain the boundary offset information in its slice header. Thereafter, the boundary offset may remain in effect for all remaining CTB lines in the picture unless such boundary offset is overridden by another boundary offset in a subsequent slice header.

The boundary offset values may be indicated in units of CTB widths.

Figure 6:
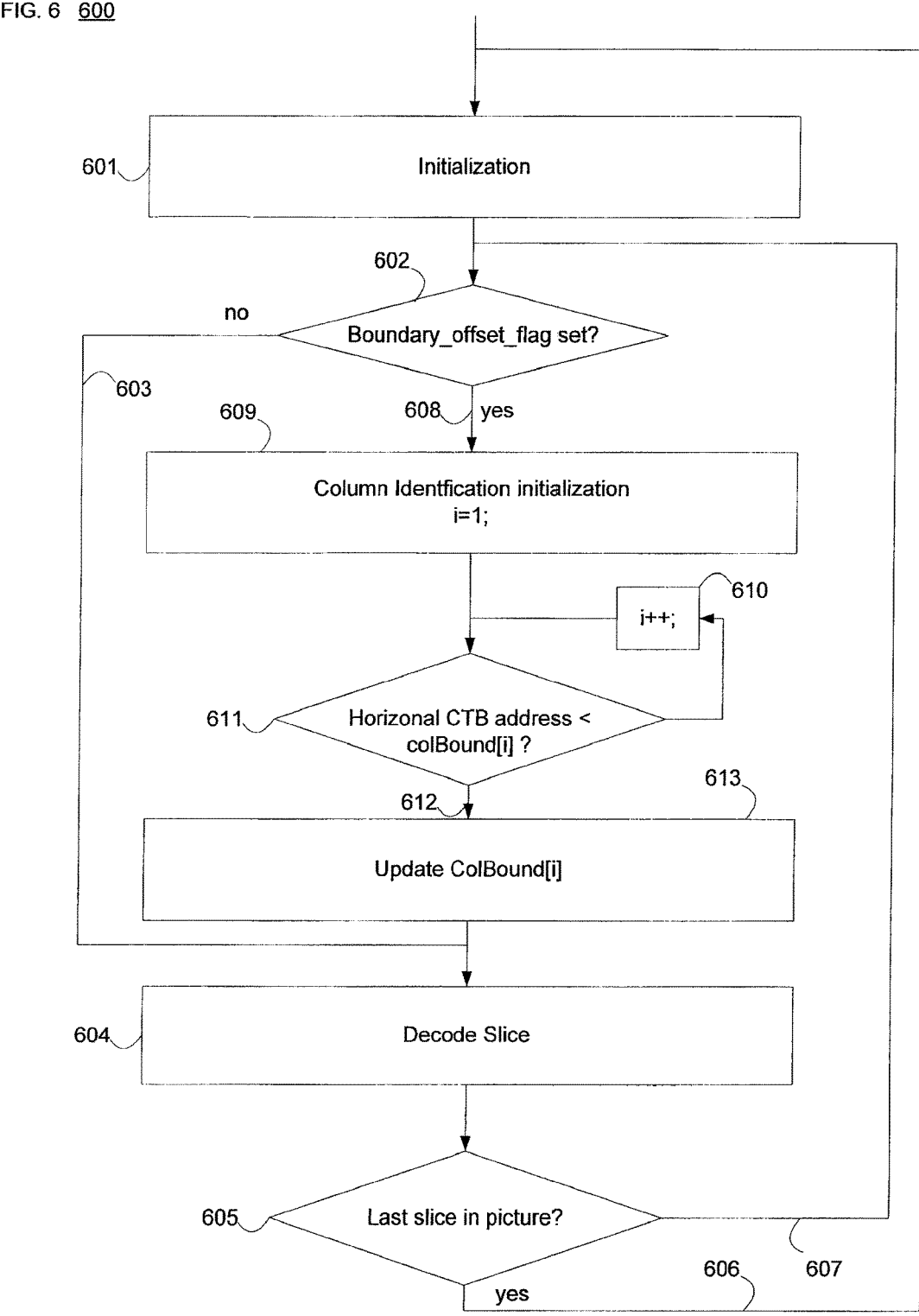
FIG. 6 is a flow diagram illustrating the operation of an exemplary decoder when decoding a slice in accordance with an embodiment of the invention.

The bitstream may contain a "boundary_offset_flag" (i.e., as seen in FIG. 6), which can be parsed from the bitstream.

If the boundary_offset_flag has a value of one, then one or both of a left_boundary_offset and right_boundary_offset may follow in the bitstream through which column boundary shifts to the right or left may be specified. Otherwise, if the boundary_offset_flag has a value of zero, then no offset values may be present in the bitstream following the boundary_offset_flag. In the style of the H.264 syntax specification, one example syntax for specifying the offset values is shown below:

```
boundary_offset_flag
if (boundary_offset_flag) {
    left_boundary_offset
    right_boundary_offset
}
```

As above, boldface variables (i.e., lines 1, 3, and 4 above), in comparison to a plain formatted line (i.e., line 2), may represent bits that are fetched from the bitstream as a side effect of or otherwise in conjunction with determining the value of the variable.

FIG. 6 is a flow diagram illustrating a method 600 that may be used to determine column boundaries based on boundary offset values parsed as above, in accordance with embodiments of the invention.

The method 600 may be initialized (601) by the following settings, which for convenience are expressed in C-style pseudo-code. Such initialization, among other things, copies the parsed boundaries from the variable columnBoundary[ ], which was derived from the high level syntax elements described above, as follows:

```
pictureWidth = width of the picture // in units of CTBs
    colBound[0] = 0;
    colBound[num_column_minus_1+1]=pictureWidth;
    for (j=1; j<num_column_minus_1+1; j++)
        colBound[j]=columnBoundary[j];
```

Thereafter, it is determined (602) whether the boundary_offset_flag (introduced above) is set. If it is determined (602) that the flag is not set, then updates of column boundaries are not allowed, and the method 600 branches (603) so that the slice is decoded (604) as previously described and specified in the video coding standard to which the decoding complies, for example, which may involve, for each CTB of the slice, processes such as entropy decoding, motion compensation to form a predictor, inverse quantization and inverse transform of coefficients to calculate a residual, adding the residual to the motion compensated predictor, in-CTB deblock-filtering the resulting samples, and so forth. Then if it is determined (605) the last slice in the picture has been decoded (a situation that can be tested by many different mechanisms, such as detecting a change in the value of the pictureID, Temporal Reference, presentation time stamp, or similar syntax element, as well as timeout mechanisms based on RTP timestamps), then the method 600 continues (606) by initializing (601) as described above to process the next picture in the bitstream. However, if it is determined (605) that the slice was not the last one of the picture, then the method 600 continues (607) by determining (602) if the boundary_offset_flag is set.

If it is determined (602) that the boundary_offset_flag is set, then the slice header contains boundary offsets that can be parsed and used to modify colBound[ ], and the method branches (608) for such modification of column boundaries. The modification may commence by an identification of the column to which the slice belongs. Such identification may in turn commence with an initialization (609), for example, which can contain instructions such as the following:

```
firstCTBMod = // first CTB of current slice modulo pictureWidth
    // where first CTB is the CTB address in scan order
leftOffset = left_boundary_offset; // as parsed
rightOffset = right_boundary_offset; // as parsed
i = 1;
```

At this point, the method 600 may search through the current state of the column boundaries (e.g., in colBound[ ]) so as to identify the particular column to which the slice being decoded belongs. For example, the method 600 may perform such identification by checking (611) the horizontal address component of the CTB address of the current CTB (which is the first CTB in the slice in question), as determined in the initialization and stored in firstCTBMod, against the stored column boundary values (colBound[ ]). By searching through the column boundaries by incrementing (610) a suitable search index, once a column boundary is identified as being located to the "right" (i.e., as having a larger horizontal address in terms of scan order) of the current slice's first CTB (as expressed in firstCTBMod), the search is finished and the method 600 exits (612) the search loop with the surviving state of the search index i.

The boundaries of the column to which the slice being decoded belongs may be updated (613), according to the surviving state of the search index i, by adding the difference information leftOffset and rightOffset, as initialized (609), to the left and right column boundaries Such updating may be achieved, for example, by the following:

colBound[i−1]=colBound[i−1]+leftOffset;

colBound[i]=colBound[i]+rightOffset;

At this point, the method 600 proceeds to the slice decoding (604) as described above.

In some case, it may be advantageous and/or convenient to impose constraints on the column boundary indication including the following constraint:

colBound[i]<colBound[i+1]

Such constraint requires columns to be numbered from the left to the right in the picture and also implies that offset values cannot be used to switch column boundary order.

The leftOffset, rightOffset and subsequently derived colBound[ ] values may also be constrained such that each resulting column has a width which is greater than or equal to a minimum column width. For example, the minimum column width may be level specific and/or specified in the video compression standard.

In some cases, the leftOffset and rightOffset may not be used to modify a colBound[ ] used as a slice boundary for a previously coded slice.

In some cases, the value of colBound[0] may not be changed from its initial value of '0' to reflect that the first numbered column begins at the leftmost edge of the picture. Consequently, the value of leftOffset would be '0' in such cases when i=1.

In some cases, the value of colBound[num_columns_minus1+1] may not be changed from its initial value of pictureWidth. Consequently, the value of rightOffset would be '0' in such cases when i=num_column_minus_1+1.

Figure 7:
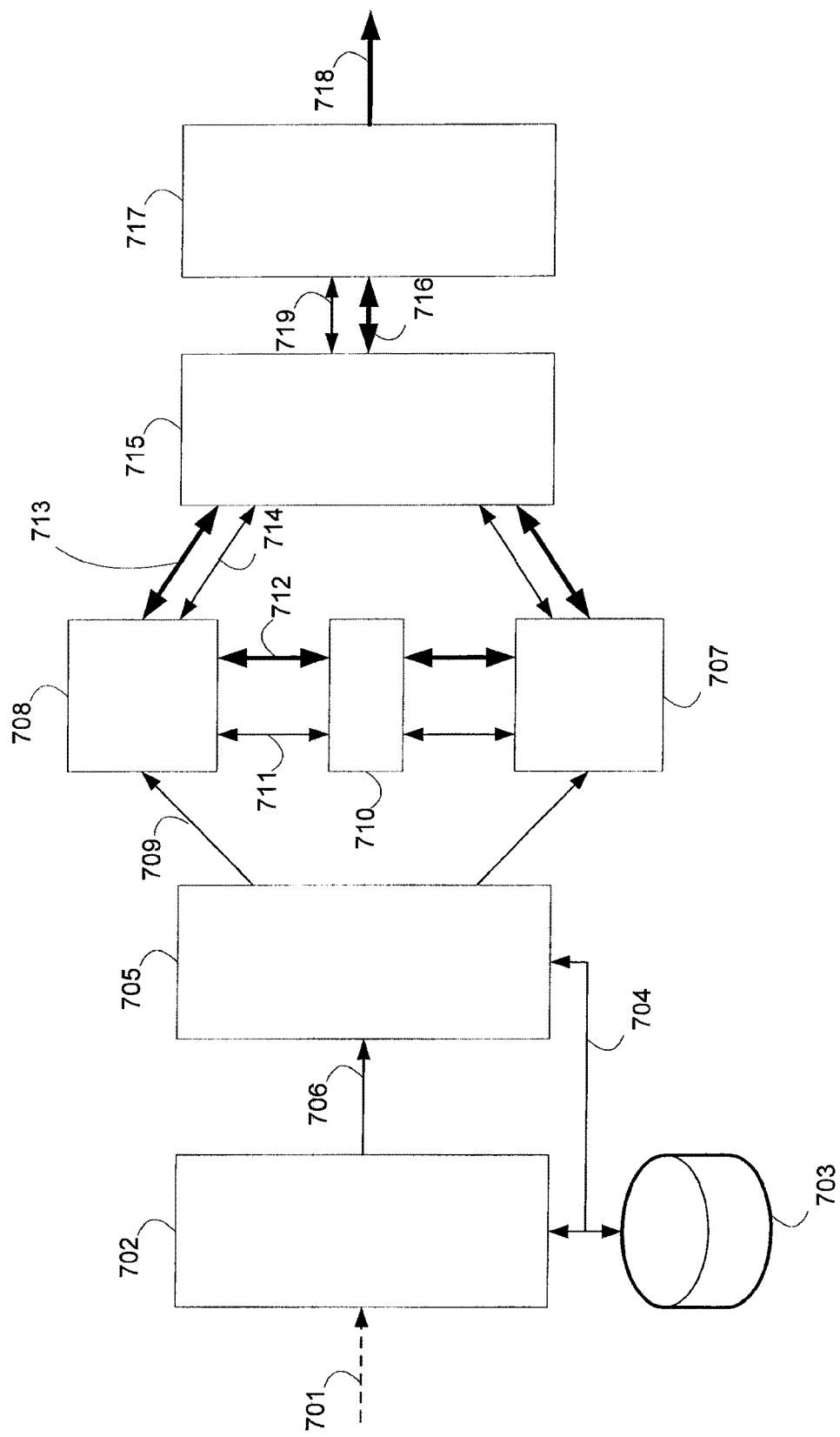
FIG. 7 is a block diagram of a decoder with two column processors in accordance with an embodiment of the invention; and, FIG. 8 is a block diagram illustrating a data processing system (e.g., a personal computer ("PC")) based implementation in accordance with an embodiment of the invention.

Referring to FIG. 7, shown is a block diagram of a decoder 700 that is based on a multiprocessor or multicore architecture in accordance with the described embodiments. For convenience, the decoder 700 is assumed to operate on a bitstream configured or made suitable for parallel decoding, for example, by requiring the use of columns with certain limitations in column width, as already described (e.g., upper and lower limits on column width).

In some embodiments, the decoder 700 can receive a coded bitstream 701 into a high level syntax interpreter 702. The bitstream 701 is shown in FIG. 7 as a punctuated line to distinguish the bitstream 701 from metadata (shown as solid hairline) and from sample data (shown in solid boldface line). The high level syntax interpreter 702 can be configured for decoding of parameter sets and subsequent storage in a parameter set database 703 to which the high level syntax interpreter 702 has read and write access. The decoded parameter sets may be stored and provided 704 to one or more other components in the decoder 700, for example, to a column/slice decoder 705. In some embodiments, the high level syntax interpreter 702 may be capable of further handling parts of, or all of, the entropy decoding of high level syntax and/or low level syntax (below CU level) elements included in the bitstream 701, which capability may depend on the assignment of entropy decoding to the column decoders 707, 708. The output data 706 of the high level syntax interpreter 702 can be, for example, metadata components derived from the bitstream 701 that can include information from the bitstream, such as symbols (created through entropy decoding) or buffers containing entropy coded symbols, as well as control information.

The column/slice decoder 705 may be coupled to the high level syntax interpreter 702 and to the parameter set database 703, and may receive the output data 706 from the high level syntax interpreter 702. In some embodiments, the column/slice decoder 705 may decode slice headers, and identify the column to which the first CTB of the slice belongs, for example, by taking into account column boundary information that can be located in parameter sets, stored in the parameter set database 703, and retrieved 704 based on the parameter set reference in the slice header. If the slice/column decoder 705 determines that a slice resides in a single column, as described above, then the column/slice decoder 705 may identify the column in which the slice resides by identifying the column to which the first CTB of the slice belongs.

Based on the column information, the column/slice decoder 705 may select one column decoder for the decoding of the slice. Two column decoders 707, 708 are shown in FIG. 7 as an example implementation of the decoder 700 and are not intended to be limiting of the possible implementations. For example, in alternatively embodiments, the encoder 700 may include a greater, or fewer, numbers of column decoders, provided the encoder 700 includes at least one column decoder. If there are more columns in the bitstream 701 than column decoders 707, 708 included in the decoder 700, then at least one of the column decoders 707, 708 may be selected for the decoding of more than one column. Alternatively, if there are more column decoders 707, 708 available in the decoder 700 than there are columns in the bitstream 701, then one or more of the column decoders 707, 708 may be idle as no column will be assigned to them by the column/slice decoder 705. However the column/slice decoder 705 may assign columns in the bitstream 701 to the column decoders 707, 708 may be handled by the column/slice decoder 705 as a load balancing problem for which many possible solutions may be apparent after familiarization with the present disclosure.

Assuming that the slice currently to be decoded is assigned to column decoder 707, data 709 required to decode the column can be forwarded to the column decoder 707. Such data 709 may have similar characteristics as output data 706 from the high level syntax interpreter 702. In some implementations, the column/slice decoder 705 may prune, or mark as irrelevant, those parts of the output data 706 that are not required for the decoding of the column, with the effect that such unneeded parts are not forwarded to column decoder 707 as part of data 709.

In some embodiments, the bitstream 701 may be configured or may otherwise allow for completely or near completely independent decoding of its content in multiple column decoders (e.g., 707 and 708 in FIG. 7). However, in other cases, some metadata or sample data information may need to be shared between multiple column decoders. Further details relevant to the nature and amount of data that may potentially need to be shared between multiple column decoders may be found in co-pending U.S. patent application Ser. No. 13/336,475.

In some embodiments, sharing of information can be handled by a suitably configured sharing unit 710. The sharing unit 701 may be implemented as shared memory, a queuing mechanism that allows message exchange, or other mechanisms for inter-processor or inter-core communication. Where information sharing is enabled by sharing unit 710, it may potentially be necessary to share both meta-information 711 (e.g., entropy decoding state, motion vector predictors) and/or sample data 712 (e.g., values of neighbouring pixels of the column used for intra prediction or motion compensation) between the column decoders 707, 708. The sharing unit 710 may also be suitably configured so as to facilitate the "handover" of information from one column decoder 707, 708 to another in such cases where a slice spans across a column boundary between adjacent columns, with the effect that multiple column decoders 707, 708 would be assigned in turn by the slice/column decoder 705 to decode such a slice.

In some embodiments, for example, in implementations of the decoder 700 that utilize a multi-processor or single multicore processor in a personal computer or similar hardware architecture, the implementation of the column decoders 707, 708 as processes running on cores or processors can be greatly facilitated by keeping all state information of the decoder 700, including for example full reference pictures, in memory that is shared between the column decoders 707, 708. In this case, the sharing unit 710 may include a shared memory aided in some cases possibly by interprocessor communication tools such as semaphores or message passing implemented, for example, in an operating system kernel.

The output of the column decoder 708 can be partly reconstructed samples 713 and associated metadata 714 provided to a combiner 715. Likewise the column decoder 707 may produce partly reconstructed samples and associated metadata, similar to partly reconstructed samples 713 and associated metadata 714 produced by column decoder 708. The samples 713 may be described as "partly" reconstructed because for full reconstruction, as specified in the video compression standard, further processing may be required in the picture-based sample generator 717, as described later. The samples 713 and associated metadata output 714 provided by column decoder 708 may be combined in the combiner 715 with the corresponding outputs of the column decoder 707 to generate a column-processed picture 716 and associated metadata 719.

The picture-based sample generator 717 may be configured so as to generate the final reconstructed picture 718 based on the column-processed picture 716 and associated metadata 719, which is received from the combiner 715. The final reconstructed picture 718 may be used possibly for output by the decoder 700 and/or as a reference picture that is fed back to other components within the decoder 700 (noted further below). The picture-based sample generator 717 can advantageously implement tasks that are not necessarily very computationally intensive, but which require access to information relating to all columns. In-loop filtering, post filtering, and error concealment are examples of those tasks. However, depending on the characteristics of the encoded bitstream 701, it may also be possible that some or all of these tasks can be implemented instead in the column decoders 707, 708 (further details of which may be found in co-pending U.S. patent application Ser. No. 13/336,475). Therefore, in some embodiments, the picture-based sample generator 717 may be omitted from the decoder 700.

Not specifically shown in FIG. 7 is the "feedback" of the reference picture samples and/or metadata to a location where the column decoder(s) 707, 708 have access to the information contained within the reference picture samples and/or metadata that be of relevance. In some embodiments, the column decoder(s) 707, 708 may be provided with associated reference picture memory, in which feedback of the reference picture samples and/or metadata may not be required. In other embodiments, the combiner 715 can may provided with a reverse data path that allows for reference picture data from the picture-based sample generator 717 to be fed back to the column decoder(s) 707, 708. In FIG. 7, such feedback path is indicated by the double-ended tips of the arrows 713, 714, 716, and 719. In still other embodiments, the reference pictures may be stored in the sharing unit 710 (in which case a corresponding data path could be provided between picture-based sample generator 717 and sharing unit 710, but not shown in FIG. 7 to enhance clarity).

Figure 8:
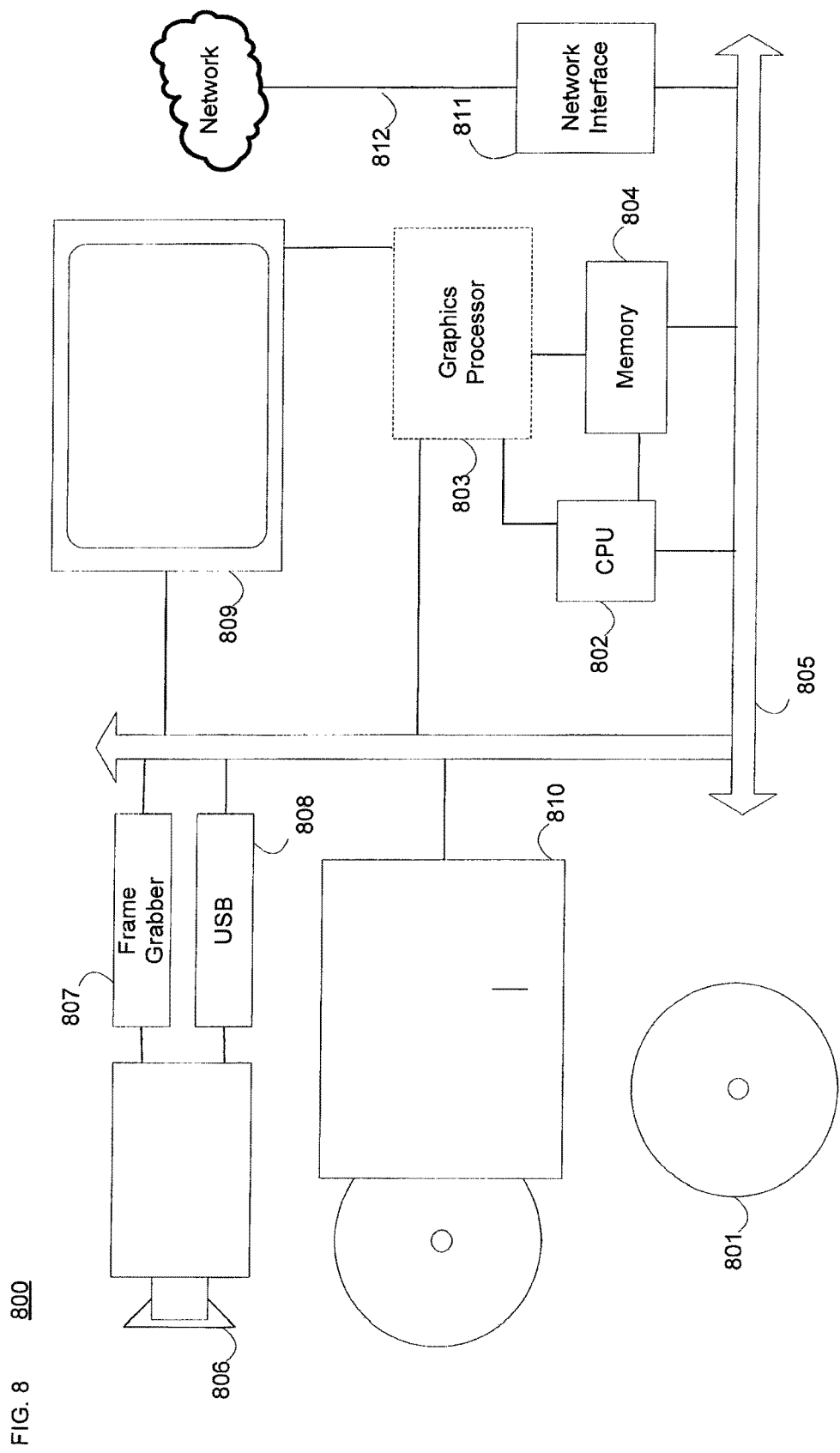

FIG. 8 is a block diagram illustrating a data processing system (e.g., a personal computer ("PC")) 800 based implementation in accordance with an embodiment of the invention. Up to this point, for convenience the description has not related explicitly to possible physical implementation of the encoder and/or decoder in detail. Many different physical implementations based on combinations of software and/or components are possible. For example, in some embodiments, the video encoder(s) and/or decoder(s) may be implemented using custom or gate array integrated circuits, in many cases, for reasons related to cost efficiency and/or power consumption efficiency.

Additionally, software based implementations are possible using general purpose processing architectures, an example of which is the data processing systems 800. For example, using a personal computer or similar device (e.g., set-top-box, laptop, mobile device), such an implementation strategy may be possible as described in the following. As shown in FIG. 8, according to the described embodiments, the encoder and/or the decoder for a PC or similar device 800 may be provided in the form of a computer-readable media 801 (e.g., CD-ROM, semiconductor-ROM, memory stick) containing instructions configured to enable a processor 802, alone or in combination with accelerator hardware (e.g., graphics processor) 803, in conjunction with memory 804 coupled to the processor 802 and/or the accelerator hardware 803 to perform the encoding or decoding. The processor 802, memory 804, and accelerator hardware 803 may be coupled to a bus 805 that can be used to deliver the bitstream and the uncompressed video to/from the aforementioned devices. Depending on the application, peripherals for the input/output of the bitstream or the uncompressed video may be coupled to the bus 805. For example, a camera 806 may be attached through a suitable interface, such as a frame grabber 807 or a USB link 808, to the bus 805 for real-time input of uncompressed video. A similar interface can be used for uncompressed video storage devices such as VTRs. Uncompressed video may be output through a display device such as a computer monitor or a TV screen 809. A DVD RW drive or equivalent (e.g., CD ROM, CD-RW Blue Ray, memory stick) 810 may be used to input and/or output the bitstream. Finally, for real-time transmission over a network 812, a network interface 811 can be used to convey the bitstream and/or uncompressed video, depending on the capacity of the access link to the network 812, and the network 812 itself.

According to various embodiments, the above described method(s) may be implemented by a respective software module. According to other embodiments, the above described method(s) may be implemented by a respective hardware module. According to still other embodiments, the above described method(s) may be implemented by a combination of software and hardware modules.

While the embodiments have, for convenience, been described primarily with reference to an example method, the apparatus discussed above with reference to a data processing system 800 may, according to the described embodiments, be programmed so as to enable the practice of the described method(s). Moreover, an article of manufacture for use with a data processing system 800, such as a pre-recorded storage device or other similar computer readable medium or product including program instructions recorded thereon, may direct the data processing system 800 so as to facilitate the practice of the described method(s). It is understood that such apparatus and articles of manufacture, in addition to the described method(s), all fall within the scope of the described embodiments.

In particular, the sequences of instructions which when executed cause the method described herein to be performed by the data processing system 800 can be contained in a data carrier product according to one embodiment of the invention. This data carrier product can be loaded into and run by the data processing system 800. In addition, the sequences of instructions which when executed cause the method described herein to be performed by the data processing system 800 can be contained in a computer program or software product according to one embodiment of the invention. This computer program or software product can be loaded into and run by the data processing system 800. Moreover, the sequences of instructions which when executed cause the method described herein to be performed by the data processing system 800 can be contained in an integrated circuit product (e.g., a hardware module or modules) which may include a coprocessor or memory according to one embodiment of the invention. This integrated circuit product can be installed in the data processing system 800.

The embodiments of the invention described herein are intended to be exemplary only. Accordingly, various alterations and/or modifications of detail may be made to these embodiments, all of which come within the scope of the invention.

What is claimed is:

1. A method for encoding in an encoder a bitstream of coded pictures, the method comprising:
    receiving an uncoded picture;
    encoding, by one or more processors, the uncoded picture into the bitstream as a first coded picture,
        wherein the first coded picture comprises a plurality of coded tree blocks (CTBs),
        wherein the first coded picture is segmented into at least two columns and at least two slices,
        wherein each CTB belongs to both a respective column and a respective slice,
        wherein a slice boundary in the first coded picture is not equal to a column boundary in the first coded picture and wherein a first slice of the at least two slices spans multiple columns, and
        wherein encoding the uncoded picture is performed using both columns and slices, and wherein encoding the uncoded picture comprises:
            for each of the plurality of slices, encoding the CTBs in the slice in an order that is based on the respective columns to which the CTBs in the slice belong, comprising during encoding of the first slice, breaking in-loop filtering within the first slice at each column boundary between adjacent columns of the multiple columns spanned by the first splice, wherein the CTBs in the first slice are decoded in an ordered sequence, first by CTB from left to right and top to bottom across all CTBs within a first column of the respective columns, and second by column from left to right across all the columns in the slice;
    encoding, by the one or more processors and in a first picture parameter set in the bitstream, a value for a number of columns N minus one for the first coded picture of the bitstream;
    encoding, by the one or more processors and in the first picture parameter set in the bitstream, column width parameters pertaining to a leftmost N−1 columns of the first coded picture, the column width parameters being measured in units of CTBs having a first size;
    encoding, by the one or more processors and in the first picture parameter set in the bitsream, a width of the first coded picture measured in units of the CTBs;
    wherein the column width parameters pertaining to the leftmost N−1 columns determine a width of a rightmost column of the first coded picture, and wherein the width of the rightmost column of the first coded picture is calculated using the width of the first coded picture in units of CTBS having the first size and the column width parameters pertaining to the N−1 leftmost columns in units of CTBs for the first coded picture; and
    transmitting, by the one or more processors, the bitstream including the first coded picture and the first picture parameter set to a decoder for reconstruction of the coded pictures in the bitstream.

2. The method of claim 1, wherein the corresponding column width of at least one column is variable between at least two rows of CTBs in the first coded picture.

3. The method of claim 2, wherein the variability is controlled by coding the corresponding column width in a slice header.

4. The method of claim 1, wherein encoding the CTBs in the slice in an order that is based on the respective columns to which the CTBs in the slice belong comprises encoding the plurality of CTBs following a scan order of CTBs, according to which the plurality of CTBs are encoded sequentially by column from left-to-right across a plurality of columns, and sequentially by CTB from left-to-right and top-to-bottom within each of the plurality of columns.

5. A method for decoding in a decoder a bitstream of coded pictures, the method comprising:

receiving the bitstream of coded pictures from an encoder;

obtaining, by one or more processors and from a first picture parameter set encoded in the bitstream, a value for a number of columns N minus one for a first coded picture of the bitstream, wherein the first coded picture comprises a plurality of coded tree blocks (CTBs), wherein the first coded picture is segmented into at least two columns and at least two slices, wherein each CTB belongs to both a respective column and a respective slice, and wherein a slice boundary in the first coded picture is not equal to a column boundary in the first coded picture and wherein a first slice of the two or more slices spans multiple columns;

obtaining, by the one or more processors and from the first picture parameter set encoded in the bitstream, column width parameters pertaining to a leftmost N−1 columns of the first coded picture, the column width parameters being measured in units having a first CTB size;

determining, by the one or more processors, a width of the first coded picture in units of the first CTB size;

calculating, by the one or more processors, a width of a rightmost column of the first coded picture using the width of the first coded picture and the column width parameters pertaining to the leftmost N−1 columns of the first coded picture; and decoding, by the one or more processors, the first coded picture using both columns and slices, the calculated width of the rightmost column of the first coded picture, and the obtained column width for the leftmost N−1 columns of the first coded picture to reconstruct a decoded image, comprising:

determining, for each of the CTBs in the first coded picture, a respective column to which the MB belongs using (i) the column width parameters obtained from the first picture parameter set encoded in the bitstream and (ii) the calculated width, and for each slice in the first coded picture, decoding the CTBs in the slice in an order that is based on the respective columns to which the CTBs in the slice belong, comprising during decoding of the first slice, breaking in-loop filtering within the first slice at each column boundary between adjacent columns of the multiple columns spanned by the first slice, wherein the CTBs in the slice are decoded in an ordered sequence, first by CTB from left to right and top to bottom across all CTBs within a first column of the respective columns, and second by column from left to right across all the columns in the slice; and outputting, by the one or more processors, the reconstructed image.

6. The method of claim 5 further comprising:

determining, from a second picture parameter set, column widths parameters pertaining to leftmost columns measured in units of a second CTB size for a second coded picture of the bitstream, the second CTB size differing from the first CTB size.

7. The method of claim 5, wherein each of the slices resides entirely within a respective column.

8. The method of claim 5, wherein sizes of the CTBs include 32×32, 16×16, and 8×8 samples.

9. The method of claim 5, wherein the rightmost column for the first coded picture spans the entire vertical height of the first coded picture.

10. A decoder for decoding a bitstream of coded pictures, the decoder comprising:

one or more computers and one or more storage devices storing instructions that are operable, when executed by the one or more computers, to cause the one or more computers to perform operations comprising:

receiving the bitstream of coded pictures from an encoder;

obtaining, from a first picture parameter set encoded in the bitstream, a value for a number of columns N minus one for a first coded picture of the bitstream, wherein the first coded picture comprises a plurality of coded tree blocks (CTBs), wherein the first coded picture is segmented into at least two columns and at least two slices, wherein each CTB belongs to both a respective column and a respective slice, and wherein a slice boundary in the first coded picture is not equal to a column boundary in the first coded picture and wherein a first slice of the two or more slices spans multiple columns;

obtaining, from the first picture parameter set encoded in the bitstream, column width parameters pertaining to a leftmost N−1 columns of the first coded picture, the column width parameters being measured in units having a first CTB size;

determining a width of the first coded picture in units of the first CTB size;

calculating a width of a rightmost column of the first coded picture using the width of the first coded picture and the column width parameters pertaining to the leftmost N−1 columns of the first coded picture; and decoding the first coded picture using both columns and slices, the calculated width of the rightmost column of the first coded picture, and the obtained column width for the leftmost N−1 columns of the first coded picture to reconstruct a decoded image, comprising:

determining, for each of the CTBs in the first coded picture, a respective column to which the MB belongs using (i) the column width parameters obtained from the first picture parameter set encoded in the bitstream and (ii) the calculated width, and for each slice in the first coded picture, decoding the CTBs in the slice in an order that is based on the respective columns to which the CTBs in the slice belong, comprising during decoding of the first slice, breaking in-loop filtering within the first slice at each column boundary between adjacent columns of the multiple columns spanned by the first slice, wherein the CTBs in the slice are decoded in an ordered sequence, first by CTB from left to right and top to bottom across all CTBs within a first column of the respective columns, and second by column from left to right across all the columns in the slice; and outputting the reconstructed image.

11. The decoder of claim 10, the operations further comprising:

determining, from a second picture parameter set, column widths parameters pertaining to leftmost columns measured in units of a second CTB size for a second coded picture of the bitstream, the second CTB size differing from the first CTB size.

12. The decoder of claim 10, wherein each of the slices resides entirely within a respective column.

13. The decoder of claim 10, wherein sizes of the CTBs include 32×32, 16×16, and 8×8 samples.

14. The decoder of claim 10, wherein the rightmost column for the first coded picture spans the entire vertical height of the first coded picture.

15. A non-transitory computer-readable medium storing software comprising instructions executable by one or more computers which, upon such execution, cause the one or more computers to perform operations comprising:
receiving the bitstream of coded pictures from an encoder;
obtaining, by one or more processors and from a first picture parameter set encoded in the bitstream, a value for a number of columns N minus one for a first coded picture of the bitstream,
wherein the first coded picture comprises a plurality of coded tree blocks (CTBs),
wherein the first coded picture is segmented into at least two columns and at least two slices,
wherein each CTB belongs to both a respective column and a respective slice, and
wherein a slice boundary in the first coded picture is not equal to a column boundary in the first coded picture and wherein a first slice of the two or more slices spans multiple columns;
obtaining, by the one or more processors and from the first picture parameter set encoded in the bitstream, column width parameters pertaining to a leftmost N−1 columns of the first coded picture, the column width parameters being measured in units having a first CTB size;
determining, by the one or more processors, a width of the first coded picture in units of the first CTB size;
calculating, by the one or more processors, a width of a rightmost column of the first coded picture using the width of the first coded picture and the column width parameters pertaining to the leftmost N−1 columns of the first coded picture; and
decoding, by the one or more processors, the first coded picture using both columns and slices, the calculated width of the rightmost column of the first coded picture, and the obtained column width for the leftmost N−1 columns of the first coded picture to reconstruct a decoded image, comprising:
determining, for each of the CTBs in the first coded picture, a respective column to which the MB belongs using (i) the column width parameters obtained from the first picture parameter set encoded in the bitstream and (ii) the calculated width, and
for each slice in the first coded picture, decoding the CTBs in the slice in an order that is based on the respective columns to which the CTBs in the slice belong, comprising during decoding of the first slice, breaking in-loop filtering within the first slice at each column boundary between adjacent columns of the multiple columns spanned by the first slice, wherein the CTBs in the slice are decoded in an ordered sequence, first by CTB from left to right and top to bottom across all CTBs within a first column of the respective columns, and second by column from left to right across all the columns in the slice; and
outputting, by the one or more processors, the reconstructed image.

16. The computer-readable medium of claim 15 the operations further comprising:
determining, from a second picture parameter set, column widths parameters pertaining to leftmost columns measured in units of a second CTB size for a second coded picture of the bitstream, the second CTB size differing from the first CTB size.

17. The computer-readable medium of claim 15, wherein each of the slices resides entirely within a respective column.

18. The computer-readable medium of claim 15, wherein sizes of the CTBs include 32×32, 16×16, and 8×8 samples.

19. The computer-readable medium of claim 15, wherein the rightmost column for the first coded picture spans the entire vertical height of the first coded picture.

20. The method of claim 1 wherein the CTBs in the first coded picture are unevenly sized.

21. The method of claim 5 wherein the CTBs in the first coded picture are unevenly sized.

22. The decoder of claim 10 wherein the CTBs in the first coded picture are unevenly sized.

23. The computer-readable medium of claim 15 wherein the CTBs in the first coded picture are unevenly sized.

* * * * *